US011166698B2

United States Patent
Takada et al.

(10) Patent No.: US 11,166,698 B2
(45) Date of Patent: Nov. 9, 2021

(54) ULTRASONIC DIAGNOSTIC APPARATUS

(71) Applicant: Toshiba Medical Systems Corporation, Otawara (JP)

(72) Inventors: Yuko Takada, Kawasaki (JP); Ryota Osumi, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 1135 days.

(21) Appl. No.: 15/010,710

(22) Filed: Jan. 29, 2016

(65) Prior Publication Data

US 2016/0220232 A1 Aug. 4, 2016

(30) Foreign Application Priority Data

Jan. 30, 2015 (JP) .............................. JP2015-017560
Jan. 22, 2016 (JP) .............................. JP2016-010478

(51) Int. Cl.
*A61B 8/08* (2006.01)
*A61B 8/00* (2006.01)
*G01S 7/52* (2006.01)

(52) U.S. Cl.
CPC .......... *A61B 8/5207* (2013.01); *A61B 8/4444* (2013.01); *A61B 8/463* (2013.01); *A61B 8/485* (2013.01); *G01S 7/52042* (2013.01); *G01S 7/52071* (2013.01)

(58) Field of Classification Search
None
See application file for complete search history.

(56) References Cited

U.S. PATENT DOCUMENTS

| 8,708,912 B2 * | 4/2014 | Osaka | A61B 8/12 600/407 |
| 2007/0112266 A1 | 5/2007 | Kishimoto | |
| 2016/0030008 A1 * | 2/2016 | Gerard | G06T 7/30 600/440 |

FOREIGN PATENT DOCUMENTS

| JP | 2-206442 A | 8/1990 |
| JP | 2004-159770 | 6/2004 |
| JP | 2005-58285 | 3/2005 |
| WO | WO 2004/089221 A1 | 10/2004 |

\* cited by examiner

*Primary Examiner* — Pascal M Bui Pho
*Assistant Examiner* — Marjan Saboktakin
(74) *Attorney, Agent, or Firm* — Oblon, McClelland, Maier & Neustadt, L.L.P.

(57) ABSTRACT

According to one embodiment, an ultrasonic diagnostic apparatus includes detection circuitry and processing circuitry. The detection circuitry detects a release state of an ultrasonic probe in an active state. The processing circuitry, when the detection circuitry detects the release state of the ultrasonic probe during activation of a control mode of generating a first image based on an output from the ultrasonic probe, displaying a second image different from the first image, and displaying the first image with a predetermined opacity on the second image, perform one of control to display the second image without generating the first image, control to display the second image without displaying the first image while generating the first image, and control to generate the first image, display the second image, and display, on the second image, the first image with an opacity lower than the predetermined opacity.

18 Claims, 17 Drawing Sheets

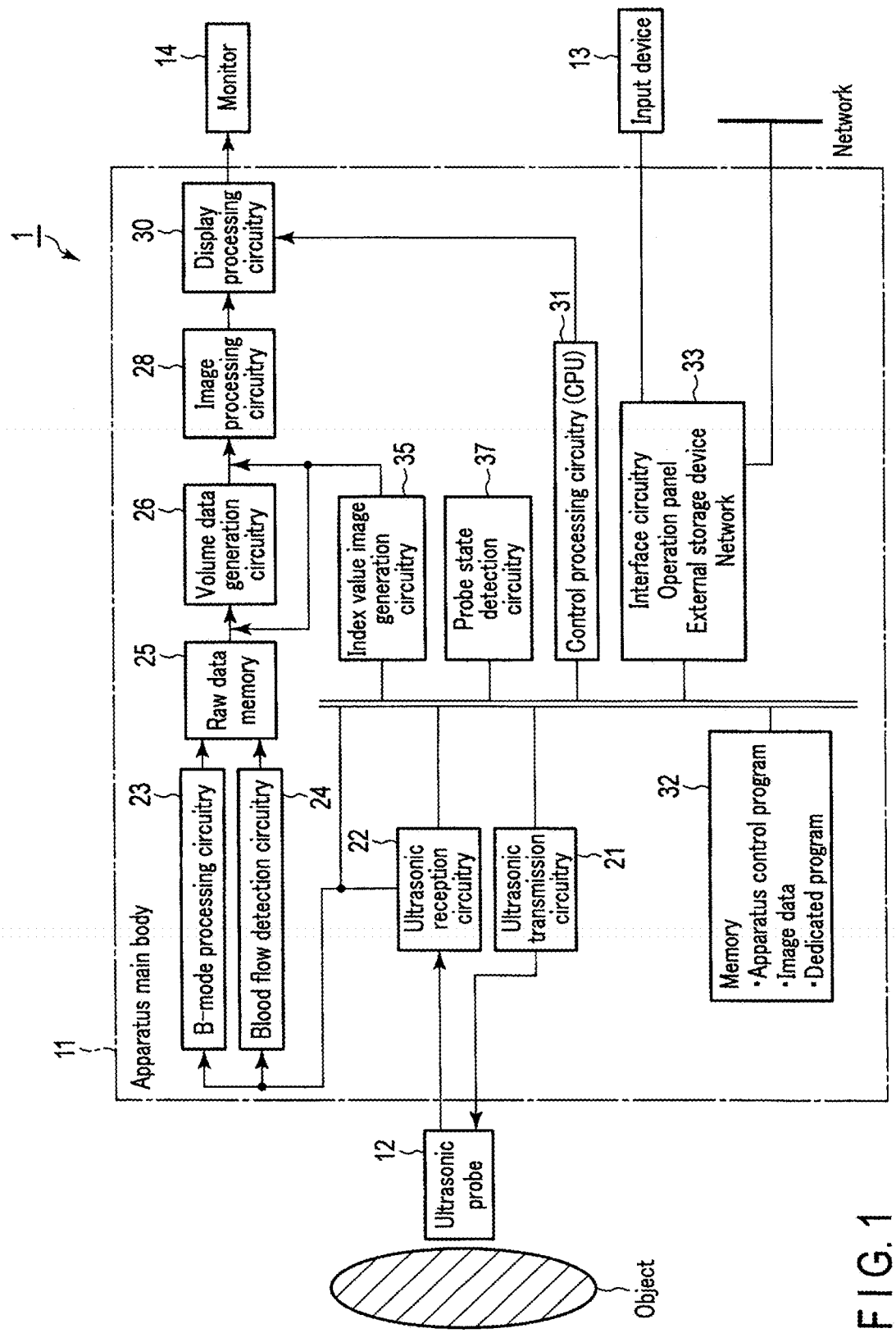
F I G. 1

FIG. 5

When all differences are smaller than threshold

|    | V0 | V1 | V2 | V3 | V4 |
|----|----|----|----|----|----|
| V0 |    | <T | <T | <T | <T |
| V1 |    |    | <T | <T | <T |
| V2 |    |    |    | <T | <T |
| V3 |    |    |    |    | <T |
| V4 |    |    |    |    |    |

FIG. 6A

When at least one difference is larger than threshold

|    | V0 | V1 | V2 | V3 | V4 |
|----|----|----|----|----|----|
| V0 |    | <T | <T | <T | <T |
| V1 |    |    | <T | <T | >T |
| V2 |    |    |    | <T | <T |
| V3 |    |    |    |    | <T |
| V4 |    |    |    |    |    |

FIG. 6B

| Region a | V0a | V1a | V2a | V3a |
|---|---|---|---|---|
| V0a | | >T | <T | >T |
| V1a | | | >T | >T |
| V2a | | | | >T |
| V3a | | | | |
FIG. 9A
| Region b | V0b | V1b | V2b | V3b |
|---|---|---|---|---|
| V0b | | <T | <T | <T |
| V1b | | | <T | <T |
| V2b | | | | <T |
| V3b | | | | |
FIG. 9B
FIG. 10
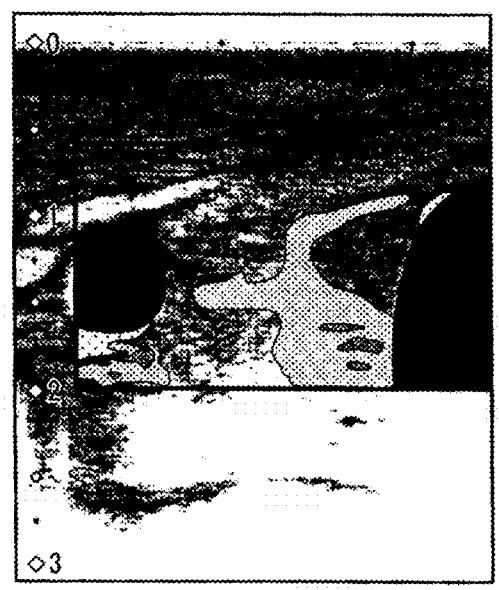
FIG. 11

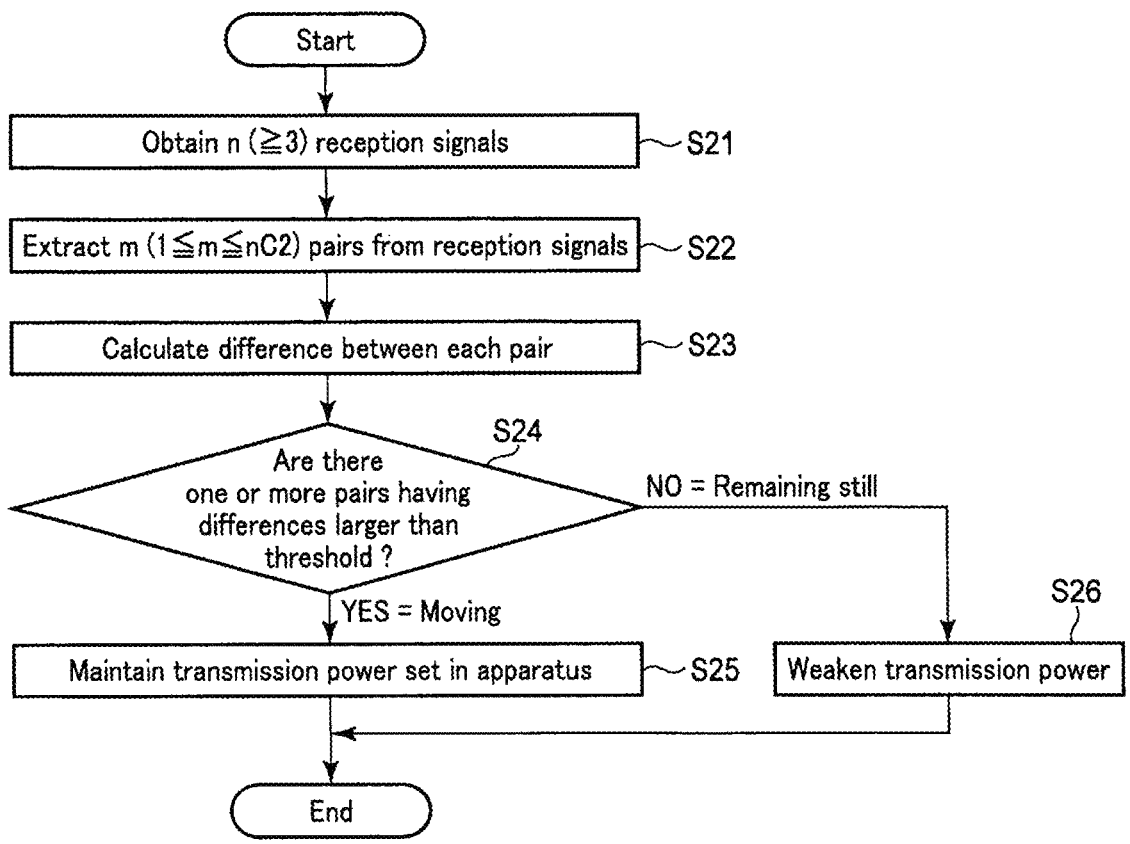
F I G. 12

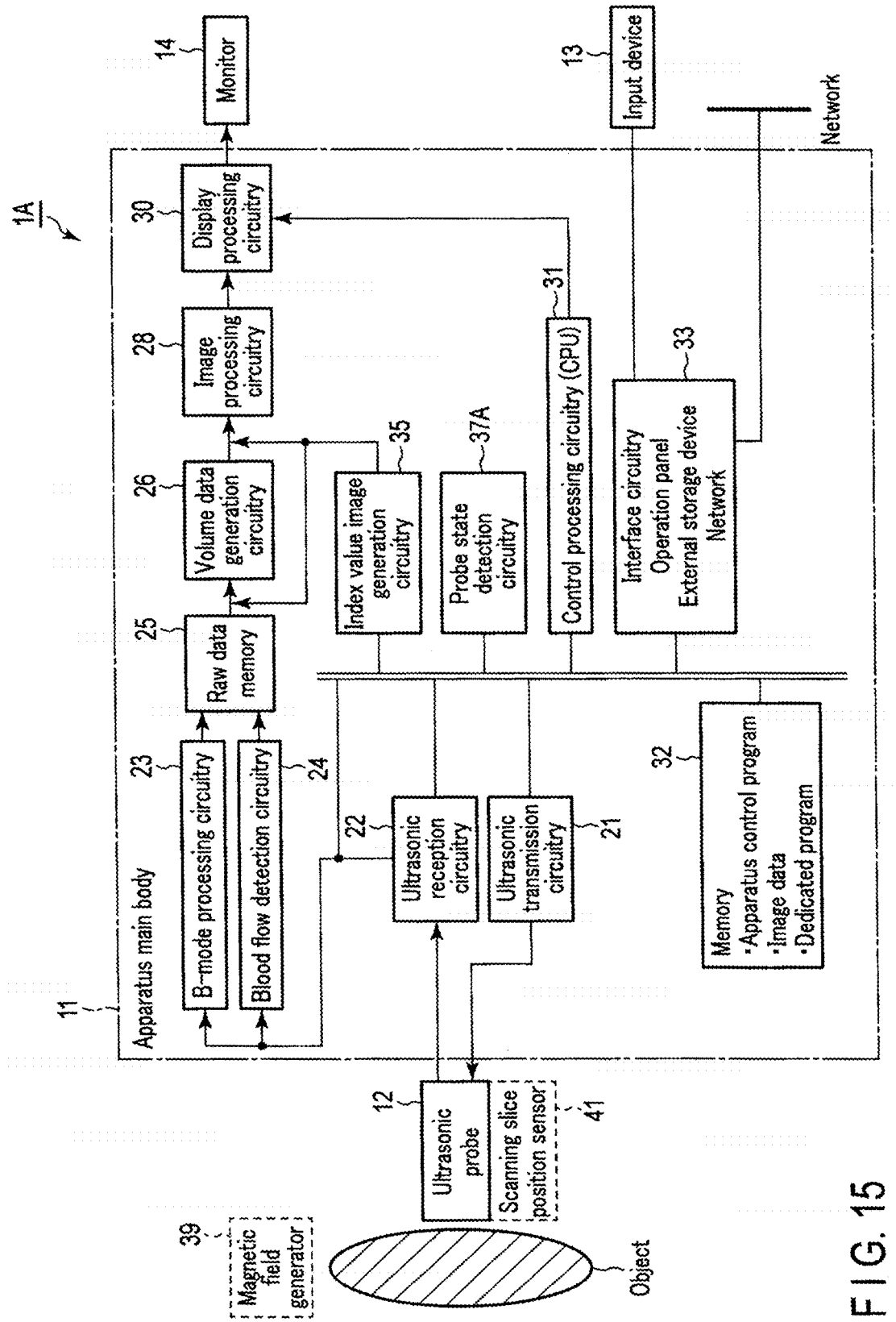
F I G. 15

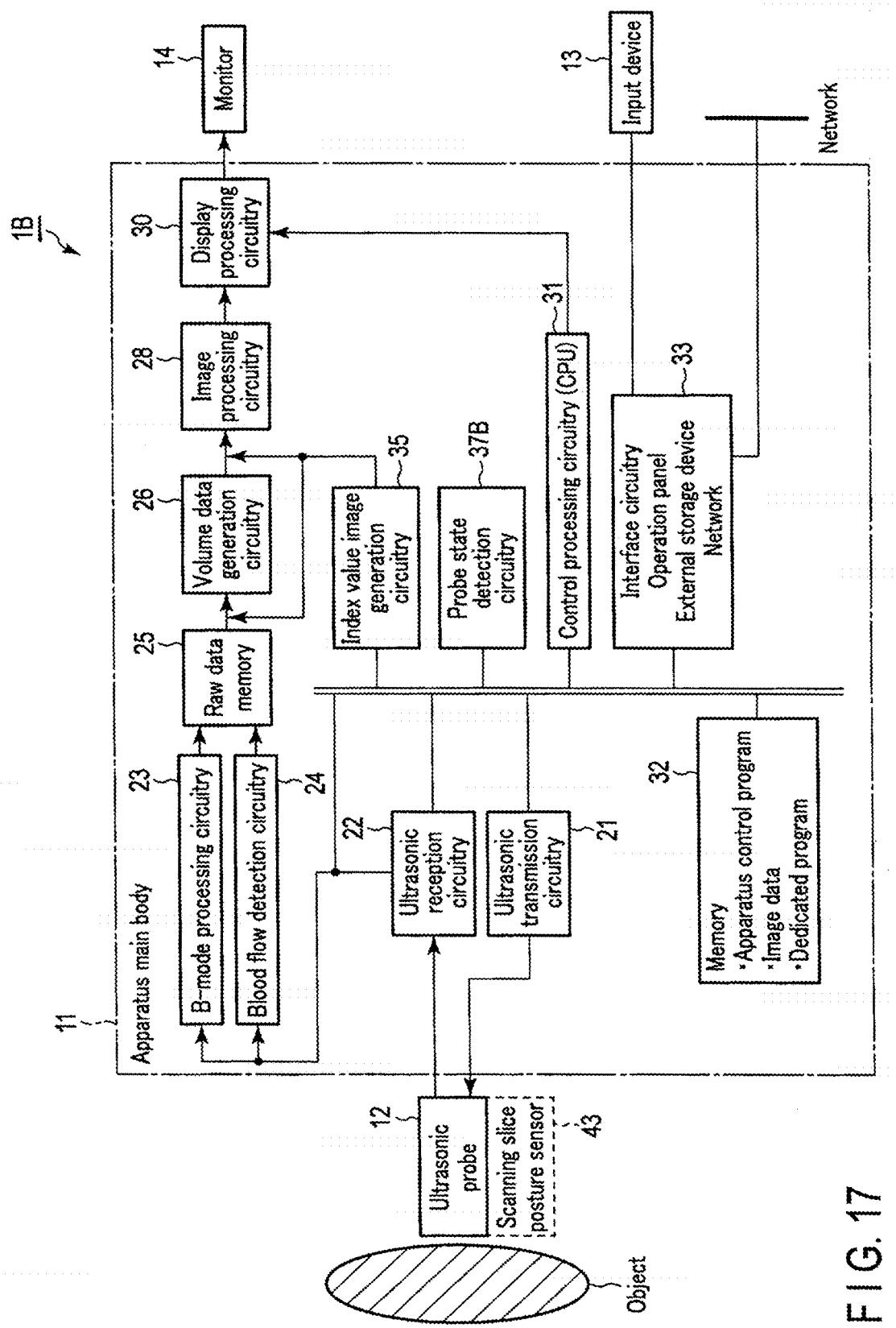
F I G. 17

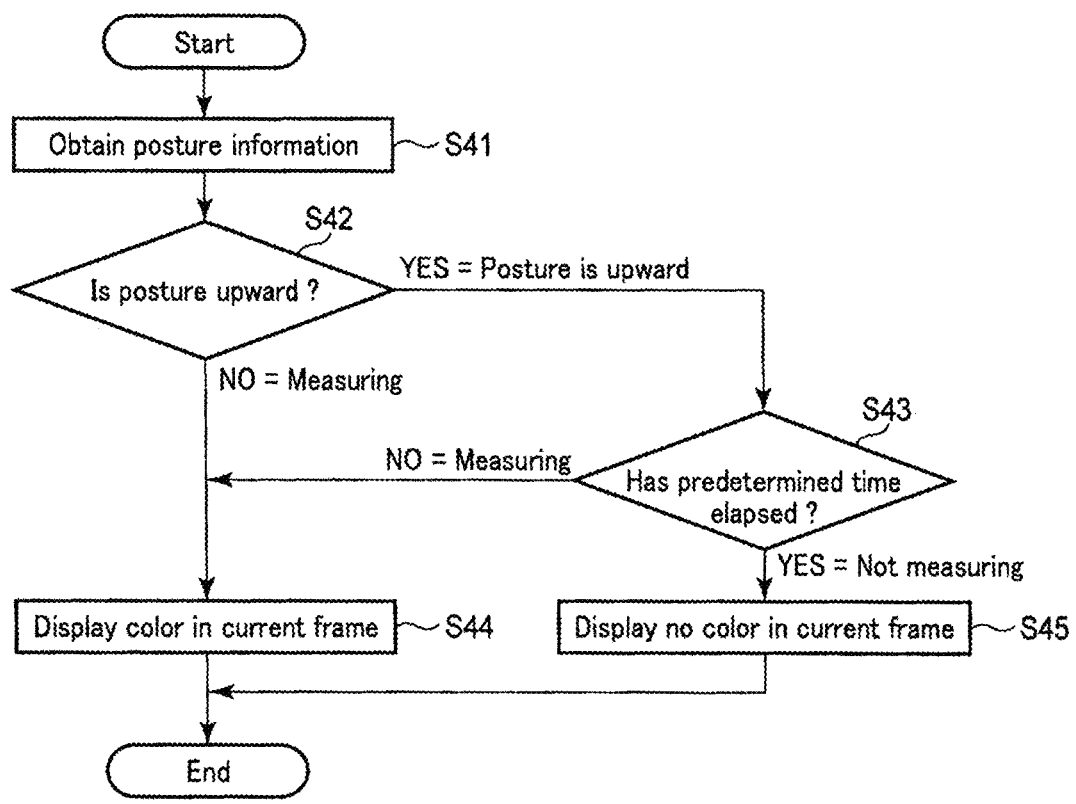
F I G. 18

ULTRASONIC DIAGNOSTIC APPARATUS

CROSS-REFERENCE TO RELATED APPLICATIONS

This application is based upon and claims the benefit of priority from the prior Japanese Patent Application No. 2015-017560, filed Jan. 30, 2015 and No. 2016-010478, filed Jan. 22, 2016, all of the entire contents of which are incorporated herein by reference.

FIELD

Embodiments described herein relate generally to an ultrasonic diagnostic apparatus used for elastic imaging.

BACKGROUND

Ultrasonic diagnosis can provide real-time display of how the heart beats or the fetus moves, by simply bringing an ultrasonic probe into contact with the body surface. This technique is highly safe, and hence allows repeated examination. Furthermore, this system is smaller in size than other diagnostic apparatuses such as X-ray, CT, and MRI apparatuses and can be moved to the bedside to be easily and conveniently used for examination. In addition, ultrasonic diagnosis is free from the influences of exposure to X-rays and the like, and hence can be used in obstetric treatment, treatment at home, and the like.

As techniques in the application field of ultrasonic diagnosis, there are available techniques of quantifying tissue characterization. Ultrasonic tissue elastic imaging (ultrasonic elastography) is one of them. This technique is designed to noninvasively measure the hardness of the entire portion or a local portion of an organ which can be detected by ultrasonic waves. Ultrasonic elastography includes several techniques such as elastography of a type that actively changes the contact pressure of an ultrasonic probe which is applied to an object by exciting the ultrasonic probe, and measures the resultant change in the body of the patient, elastography of a type that measures a change in the body of a patient which is caused by a biological function such as respiratory movement or cardiac pulsation without greatly changing the contact pressure of an ultrasonic probe, and elastography of a type that measures a change in the body of a patient which is caused by an acoustic radiation force.

Such ultrasonic elastography colorizes physical amounts such as displacements or velocities at positions in, for example, an ROI (Region Of Interest) as index values (kinetic information) in accordance with the values of the physical amounts and overlay-displays the resultant image on a tissue structure image such as a B-mode image. An observer such as a doctor can observe in real time the tissue structures of overlay-displayed diagnosis regions and kinetic information generated at each region by manual vibration or the like.

Assume that elastography is to be performed by manual vibration. In this case, while an ultrasonic probe is left released in the air (to be simply referred to as an "release state" hereinafter), since a target having a velocity is not imaged, no kinetic information should be theoretically colorized and overlay-displayed on a tissue structure image.

In practice, however, even in the release state, velocity information originating from a noise signal or the like is sometimes detected and colorized, and the resultant image sometimes overlay-displayed, as shown in, for example, FIG. 13A. If, however, an ultrasonic probe is in the release state while being coated with gel, fine vibration originating from, for example, an apparatus is conducted to the ultrasonic probe through the gel. As a result, the vibration is detected and colorized in spite of no manual vibration, and the resultant image is sometimes overlay-displayed, as shown in, for example, FIG. 13B.

If information which has originated from the apparatus or the like and is irrelevant to manual vibration is colorized and overlay-displayed, this may cause a user or patient to feel anxiety about image diagnosis using the ultrasonic elastography. For this reason, for example, the following contrivances have been applied to conventional ultrasonic diagnostic apparatuses so as to inhibit information irrelevant to manual vibration from being color-displayed even while the ultrasonic probe is in the release state. That is, as shown in FIG. 14, ratio Vr=V0/Vmax is calculated, where V0 is an average velocity in an ROI set in the current frame and Vmax is the maximum velocity (a value in a currently set velocity range (scale)) which can be detected in the currently set velocity range. If the calculated value is equal to or less than a predetermined threshold (Tresh), it is determined that the ultrasonic probe is in the release state, and color display concerning the interior of the ROI is inhibited.

BRIEF DESCRIPTION OF THE DRAWING

FIG. 1 is a block diagram showing the arrangement of an ultrasonic diagnostic apparatus 1 according to an embodiment;

FIG. 5 is a view for explaining all the combinations of average velocities V0, V1, V2, V3, and V4 corresponding to five frames;

FIGS. 6A and 6B are views for explaining the details of determination processing by a probe state detection circuitry 37 in step S15;

FIGS. 9A and 9B are views for explaining the details of determination processing by a probe state detection circuitry 37 according to a modification;

FIG. 10 is a view showing an example of an elastography image displayed in a conventional ultrasonic diagnostic apparatus;

FIG. 11 is a view for explaining an elastography image displayed by display control using a probe state detection function according to this modification;

FIG. 12 is a flowchart showing a display control procedure using a probe state detection function according to the second embodiment;

FIG. 15 is a block diagram showing the arrangement of an ultrasonic diagnostic apparatus according to the third embodiment;

FIG. 17 is a block diagram showing the arrangement of an ultrasonic diagnostic apparatus according to the fourth embodiment;

FIG. 18 is a flowchart showing a display control procedure using a probe state detection function according to the fourth embodiment;

DETAILED DESCRIPTION

Figure 2:
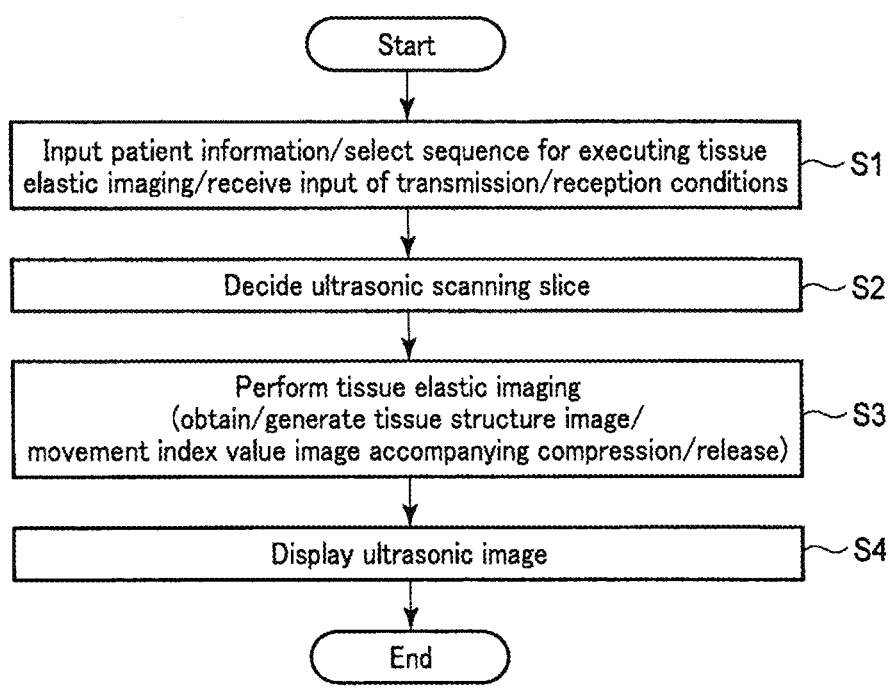
FIG. 2 is a flowchart showing a processing procedure in typical tissue elastic imaging.

According to one embodiment, an ultrasonic diagnostic apparatus includes detection circuitry and processing circuitry. The detection circuitry detects a release state of an ultrasonic probe in an active state. The processing circuitry, when the detection circuitry detects the release state of the ultrasonic probe during activation of a control mode of generating a first image based on an output from the ultrasonic probe, displaying a second image different from the first image, and displaying the first image with a predetermined opacity on the second image, perform one of control to display the second image without generating the first image, control to display the second image without displaying the first image while generating the first image, and control to generate the first image, display the second image, and display, on the second image, the first image with an opacity lower than the predetermined opacity.

The embodiments will be described below with reference to the accompanying drawing. Note that the same reference numerals in the following description denote constituent elements having almost the same functions and arrangements, and a repetitive description will be made only when required.

FIG. 1 is a block diagram showing the arrangement of an ultrasonic diagnostic apparatus 1 according to an embodiment. As shown in FIG. 1, the ultrasonic diagnostic apparatus 1 includes an ultrasonic diagnostic apparatus main body 11, an ultrasonic probe 12, an input device 13, and a monitor 14. The ultrasonic diagnostic apparatus main body 11 includes an ultrasonic transmission circuitry 21, an ultrasonic reception circuitry 22, a B-mode processing circuitry 23, a blood flow detection circuitry 24, a raw data memory 25, a volume data generation circuitry 26, an image processing circuitry 28, a display processing circuitry 30, a control processing circuitry 31, a memory 32, an interface unit 33, an index value image generation circuitry 35, and a probe state detection circuitry 37.

The ultrasonic probe 12 is a device (probe) which transmits ultrasonic waves to an object, typically a living body, and receives reflected waves from the object based on the transmitted ultrasonic waves. The ultrasonic probe 12 has, on its distal end, an array of a plurality of piezoelectric transducers (ultrasonic transducers), a matching layer, a backing member, and the like. The piezoelectric transducers transmit ultrasonic waves in a desired direction in a scanning region based on driving signals from the ultrasonic transmission circuitry 21, and convert reflected waves from the object into electrical signals. The matching layer is an intermediate layer which is provided for the piezoelectric transducers to make ultrasonic energy efficiently propagate. The backing member prevents ultrasonic waves from propagating backward from the piezoelectric transducers. When the ultrasonic probe 12 transmits an ultrasonic wave to an object, the transmitted ultrasonic wave is sequentially reflected by a discontinuity surface of acoustic impedance of internal body tissue, and is received as an echo signal by the ultrasonic probe 12. The amplitude of this echo signal depends on an acoustic impedance difference on the discontinuity surface by which the echo signal is reflected. The echo produced when a transmitted ultrasonic pulse is reflected by a moving blood flow is subjected to a frequency shift depending on the velocity component of the moving body in the ultrasonic transmission/reception direction by the Doppler effect. Note that in this embodiment, the ultrasonic probe 12 is a one-dimensional array probe having a plurality of ultrasonic transducers arrayed along a predetermined direction. However, this is not exhaustive. The ultrasonic probe 12 may be a two-dimensional array probe (a probe having a plurality of ultrasonic transducers arrayed in the form of a two-dimensional matrix) or a mechanical 4D probe (a probe which can execute ultrasonic scanning while mechanically swinging an ultrasonic transducer array in a direction perpendicular to the array direction).

The input device 13 is connected to the apparatus main body 11 and includes various types of switches, buttons, a trackball, a mouse, and a keyboard which are used to input, to the apparatus main body 11, various types of instructions, conditions, an instruction to set an ROI (Region Of Interest), various types of image quality condition setting instructions, and the like from an operator.

The monitor 14 displays morphological information and blood flow information in the living body as images based on video signals from the display processing circuitry 30. The monitor 14 displays an elastography image, for which execution/non-execution of color display is controlled in accordance with whether the ultrasonic probe is in the release state, in tissue elastic imaging.

The ultrasonic transmission circuitry 21 includes trigger generation circuitry, delay circuitry, and puller circuitry (none of which are shown). The trigger generation circuitry repeatedly generates trigger pulses for the formation of transmission ultrasonic waves at a predetermined rate frequency fr Hz (period: 1/fr sec). The delay circuitry gives each trigger pulse a delay time necessary to focus an ultrasonic wave into a beam and determine transmission directivity for each channel. The pulser circuitry applies a driving pulse of a predetermined voltage to the probe 12 at the timing based on this trigger pulse.

The ultrasonic reception circuitry 22 includes amplifier circuitry, an A/D converter, delay circuitry, and an adder (none of which are shown). The amplifier circuitry amplifies an echo signal received via the probe 12 for each channel. The A/D converter converts each amplified analog echo signal into a digital echo signal. The delay circuitry gives the digitally converted echo signals delay times necessary to determine reception directivities and perform reception dynamic focusing. The adder then performs addition processing for the signals. With this addition, a reflection component from a direction corresponding to the reception directivity of the echo signal is enhanced to form a composite beam for ultrasonic transmission/reception in accordance with reception directivity and transmission directivity.

The B-mode processing circuitry 23 is constituted by, for example, a predetermined processor and a memory. The B-mode processing circuitry 23 receives an echo signal from the reception circuitry 22, and performs logarithmic amplification, envelope detection processing, and the like for the signal to generate data whose signal intensity is expressed by a luminance level.

The blood flow detection circuitry 24 is constituted by, for example, a predetermined processor and a memory. The blood flow detection circuitry 24 extracts a blood flow signal from the echo signal received from the reception circuitry 22, and generates blood flow data. The blood flow detection circuitry 24 generally extracts a blood flow by CFM (Color Flow Mapping). In this case, the blood flow detection circuitry 24 analyzes the blood flow signal to obtain blood flow information such as mean velocities, variances, and powers as blood flow data at multiple points.

The raw data memory 25 generates B-mode raw data as B-mode data on three-dimensional ultrasonic scanning lines by using a plurality of B-mode data received from the B-mode processing circuitry 23. The raw data memory 25 also generates blood flow raw data as blood flow data on three-dimensional ultrasonic scanning lines by using a plurality of blood flow data received from the blood flow detection circuitry 24. Note that for the purpose of reducing noise or smooth concatenation of images, a three-dimensional filter may be inserted after the raw data memory 25 to perform spatial smoothing.

The volume data generation circuitry 26 is constituted by, for example, a predetermined processor and a memory. The volume data generation circuitry 26 generates B-mode volume data or blood flow volume data by executing raw-voxel conversion including interpolation processing in consideration of spatial position information.

The image processing circuitry 28 is constituted by, for example, a predetermined processor and a memory. The image processing circuitry 28 performs predetermined image processing such as volume rendering, MPR (Multi Planar Reconstruction), and MIP (Maximum Intensity Projection) for the volume data received from the volume data generation circuitry 26. Note that for the purpose of reducing noise or smooth concatenation of images, a two-dimensional filter may be inserted after the image processing circuitry 28 to perform spatial smoothing.

The display processing circuitry 30 is constituted by, for example, a predetermined processor and a memory. The display processing circuitry 30 executes various types of processing associated with a dynamic range, luminance (brightness), contrast, γ curve correction, RGB conversion, and the like for various types of image data generated/processed by the image processing circuitry 28. In addition, in tissue elastic imaging, the display processing circuitry 30 executes display control for mapping index values at positions in an arbitrarily set ROI (to be referred to as an "elastography ROI" or simply "ROI" hereinafter) to corresponding positions on a tissue structure image such as a B-mode image by using an index value image generated for each frame by the index value image generation circuitry 35, and performing color display (overlay-display) in accordance with the index values. The display processing circuitry 30 also executes control concerning the execution/non-execution of color display in accordance with whether the ultrasonic probe is in the release state in display control using a probe state detection function (to be described later). Note that it is possible to control execution/non-execution of color display by, for example, controlling the opacity of each of pixels color-mapped in an ROI or controlling execution/non-execution of color mapping of index values at positions in an ROI.

The control processing circuitry 31 is constituted by, for example, a predetermined processor and a memory. The control processing circuitry 31 has the function of an information processing apparatus (computer) and controls the operation of each constituent element. The control processing circuitry 31 executes display control using the probe state detection function (to be described later) and control concerning transmission by the ultrasonic probe using the probe state detection function.

The memory 32 stores a program for implementing display control using the probe state detection function (to be described later) or control concerning transmission by the ultrasonic probe using the probe state detection function, a diagnosis protocol, transmission/reception conditions, and other data groups. The memory 32 is also used to archive images in an image memory (not shown), as needed. It is possible to transfer data in the memory 32 to an external peripheral device via the interface unit 33.

The interface unit 33 is an interface concerning the input device 13, a network, and a new external storage device (not shown). The interface unit 33 includes an input interface circuitry and a network interface circuitry (none of which are shown). Another apparatus can also be connected to the ultrasonic diagnostic apparatus main body 11 via the interface unit 33. In addition, the interface unit 33 can transfer data such as ultrasonic images, analysis results, and the like obtained by this apparatus to other apparatuses via the network.

The index value image generation circuitry 35 is constituted by, for example, a predetermined processor and a memory. The index value image generation circuitry 35 executes tracking processing using, for example, time-series B-mode images and generates an index value image indicting the two-dimensional distribution of index values (e.g., velocities, displacements, distortions, or distortion rates, to be simply referred to as index values hereinafter) indicating the movement of a tissue by using the tracking processing result. In addition, the index value image generation circuitry 35 calculates index values by frequency-analyzing a Doppler signal obtained by, for example, a tissue Doppler mode, and generates an index value image by using the index values. The index value image generation circuitry 35 can further calculate index values indicating the movement of the tissue by correlation processing using an echo signal (RF signal or I/Q signal). Note that for a concrete description, this embodiment will exemplify a case in which tracking processing is executed by using a plurality of B-mode images, and an index value image indicating the two-dimensional distribution of index values is generated by using the tracking processing result.

The probe state detection circuitry 37 is constituted by, for example, a predetermined processor and a memory. The probe state detection circuitry 37 calculates the time-series index values of a tissue and changes in the time-series index values and discriminates/detects the release state and non-release state of the ultrasonic probe 12. This operation of the probe state detection circuitry 37 will be described in detail later.

(Display Control Using Probe State Detection Function)

FIG. 2 is a flowchart showing a processing procedure in typical tissue elastic imaging. As shown in FIG. 2, in tissue elastic imaging, the following steps are executed: input patient information, select a sequence for executing a tissue elastic imaging, receive the input of transmission/reception conditions, and receive the input of an imaging start instruction (step S1); decide an ultrasonic scanning slice (step S2); obtain/generate a tissue structure image/index value image accompanying compression/release (step S3); and display an ultrasonic image (step S4).

In addition, in tissue elastic imaging based on these series of processing, the ultrasonic probe is sometimes set in a state in which it is released in the air (to be simply referred to as "release state" hereinafter) without applying any manual vibration to a diagnosis region, as needed.

Display control using the probe state detection function is executed such that this release state and a state (non-release state) in which, for example, an ultrasonic image is obtained by using the ultrasonic probe while manual vibration is applied to a diagnosis region are discriminated/detected, and color display of an index value image on an ultrasonic image displayed as an elastography image is "not executed" upon detection of the release state.

Note that display control using the probe state detection function is repeatedly executed concurrently with steps S2 and S3 in response to the input of an imaging start instruction in step S1 as a trigger, thereby controlling display of an ultrasonic image in step S4.

Figure 3:
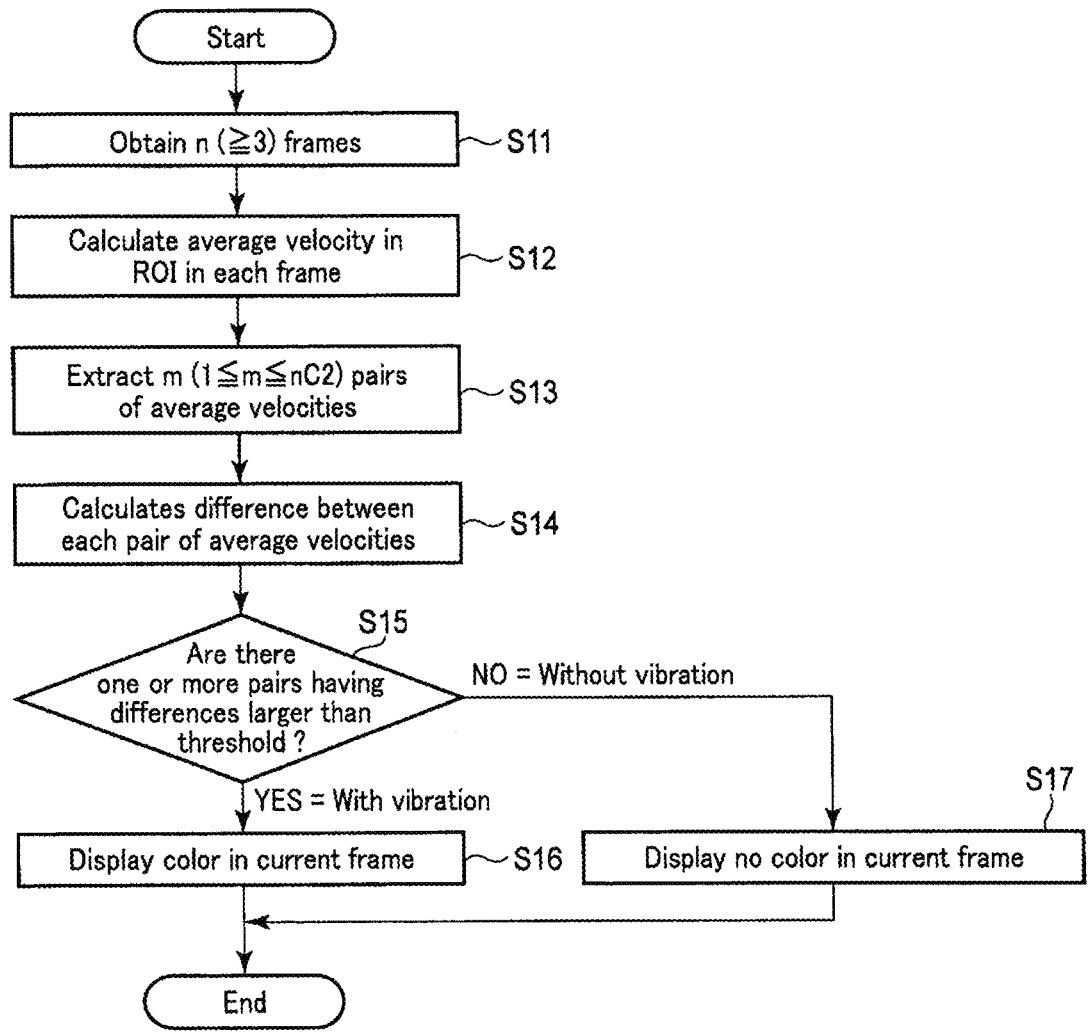
FIG. 3 is a flowchart showing a display control procedure using a probe state detection function.

FIG. 3 is a flowchart showing a display control procedure using the probe state detection function. Processing in each step will be described below with reference to FIG. 3.

Time-series index value images are sequentially obtained at a predetermined frame rate by ultrasonic transmission/reception executed in response to the input of an imaging start instruction in step S1 in FIG. 2 as a trigger (in this embodiment, each temporal section (one unit) of time-serially obtained images is called a "frame"). The probe state detection circuitry 37 obtains a plurality of index value images corresponding to n (n is an integer satisfying n≥3) frames obtained over a predetermined period of the time-serially obtained index value images (step S11). Note that n frames are preferably temporally continuous, but not limited to it. For example, when making observation in a long span without increasing the amount of data processed, it is possible to use a discontinuous extraction method of, for example, picking up a total of five frames by picking up one frame for every three frames. Assume that in this embodiment, for a concrete description, index value images corresponding to a total of five frames (i.e., n=5) are obtained, including the current frame and four frames preceding the current frame.

Figure 4:
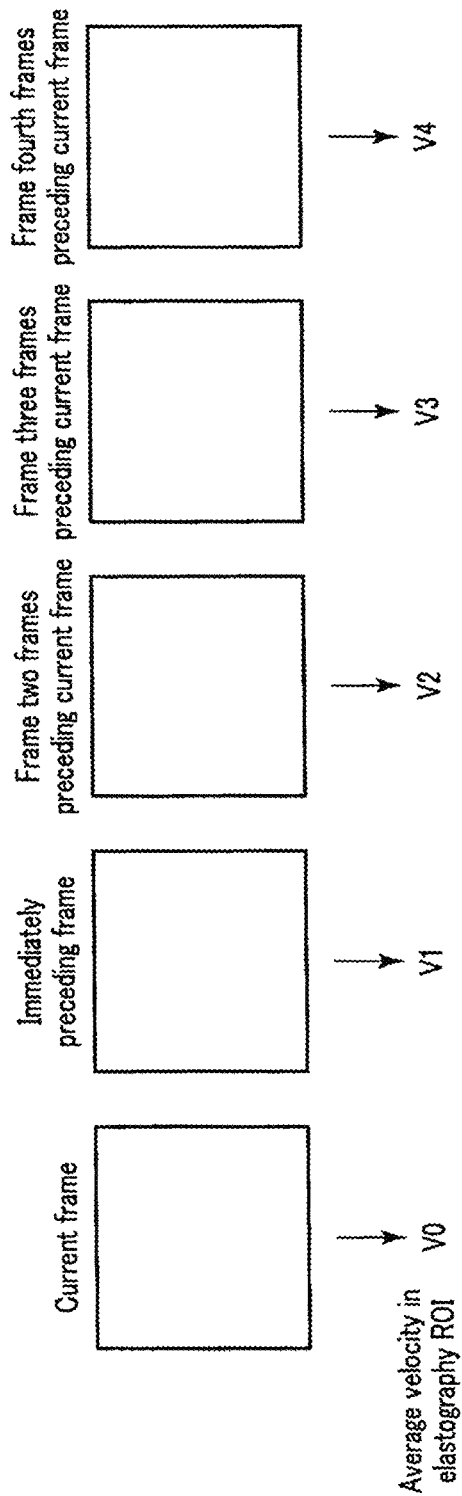
FIG. 4 is a view exemplarily showing ROIs respectively set in time-serially obtained index value images and average velocities in the respective ROIs.

The probe state detection circuitry 37 respectively sets ROIs in a plurality of index value images corresponding to obtained five frames, as shown in FIG. 4, and calculates statistics (average velocities in this case) in the respective ROIs (step S12). Note that in the case shown in FIG. 4, the average velocity in the ROI in the current frame is represented by V0, and the average velocities in the ROIs in the respective frames are respectively represented by V1, V2, V3, and V4 as the frames go back from the current frame one by one. Note that statistics calculated in the ROIs by the probe state detection circuitry 37 are not limited to the average values of physical amounts such as velocities, and may be medians, variances, maximum values, minimum values, or the like The probe state detection circuitry 37 extracts desired m (m is an integer satisfying 1≤m≤5C2) combinations of two of V0, V1, V2, V3, and V4 corresponding to the five frames, and calculates the absolute value of the difference value between each extracted combination (pair) of average velocities (steps S22 and S23). If, for example, m=5C2=10, the probe state detection circuitry 37 extracts all the combinations shown in FIG. 5 by using V0, V1, V2, V3, and V4 corresponding to the five frames, and calculates the absolute values of the difference values (to be simply referred to as "difference values" hereinafter) between average velocities corresponding to all the combinations. For example, the probe state detection circuitry 37 calculates a difference value |V0−V3| corresponding to a combination corresponding to the hatched portion in FIG. 5, and calculates a difference value |V2−V4| corresponding to a combination corresponding to the dot region.

The probe state detection circuitry 37 then compares each difference value corresponding to each combination obtained in step S14 with a predetermined threshold T, and determines, based on the comparison results, whether there is one or more difference values larger than the predetermined threshold T (step S15). More specifically, as shown in FIG. 6A, if all the difference values corresponding to all the combinations are smaller than the predetermined threshold T, the probe state detection circuitry 37 determines that "the release state of the ultrasonic probe is detected", and sends out a signal indicating the corresponding information to the control processing circuitry 31 (NO in step S24=(ultrasonic probe) remaining still). On the other hand, as shown in FIG. 6B, if at least one of all the difference values corresponding to all the combinations is equal to or more than the predetermined threshold (in the case shown in FIG. 6B, |V1−V4|>T), the probe state detection circuitry 37 determines that "the release state of the ultrasonic probe is not detected", and sends out a signal indicating the corresponding information to the control processing circuitry 31 (YES in step S24=(ultrasonic probe) moving).

The control processing circuitry 31 controls the display processing circuitry 30 to as to display a color image in an ROI in an index value image in elastography corresponding to the current frame upon reception of the signal indicating "the release state of the ultrasonic probe is not detected" from the probe state detection circuitry 37 (step S16). In contrast, upon reception of the signal indicating "the release state of the ultrasonic probe is detected" from the probe state detection circuitry 37, the control processing circuitry 31 controls the display processing circuitry 30 so as not to display any color image in an ROI in an index value image in elastography corresponding to the current frame (step S17).

Figure 7B:
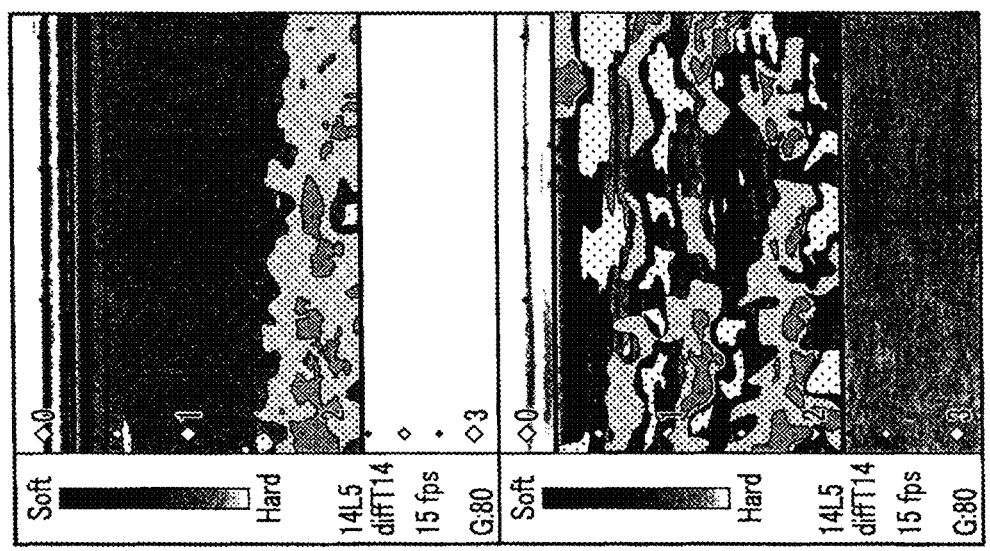
FIGS. 7A and 7B are views for explaining elastography for which display control is performed so as not to display any color image in an ROI in an index value image corresponding to the current frame in step S17 upon determination in step S15 that "the release state of the ultrasonic probe is detected"
Figure 7A:
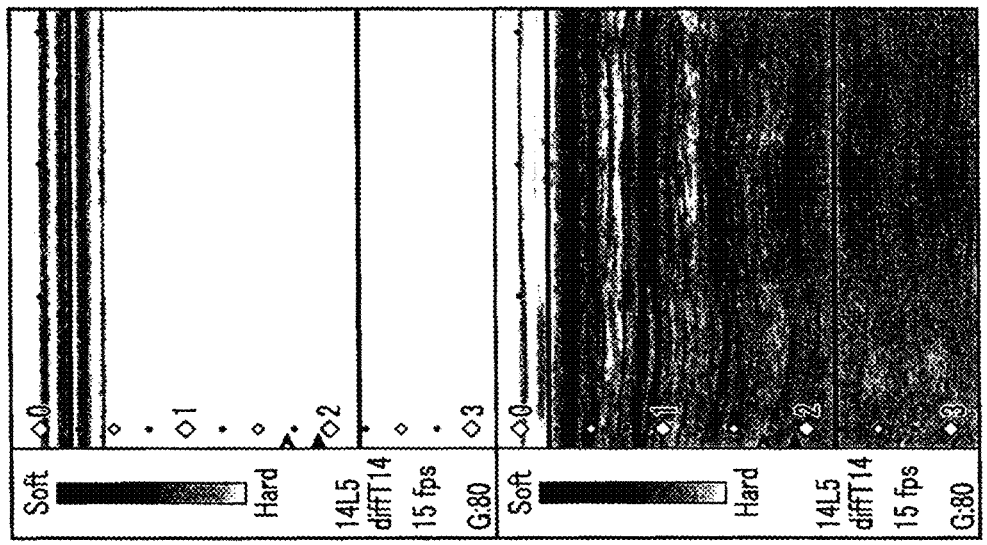

FIG. 7A is a view showing an example of an elastography image displayed in the release state in a conventional ultrasonic diagnostic apparatus. FIG. 7B is a view for explaining elastography subjected to display control so as to determine that "the release state of the ultrasonic probe is detected" in step S15 and so as not to display any color image in an ROI in an index value image corresponding to the current frame in step S17. In either of the cases shown in FIGS. 7A and 7B, the upper portion indicates the release state with "the ultrasonic probe being coated with no gel", and the lower portion indicates the release state with "the ultrasonic probe being coated with gel".

As shown in FIG. 7B, as a result of display control in step S17, if the "release state" is detected regardless of whether the detected state is the release state with "the ultrasonic probe being coated with no gel" or the release state with "the ultrasonic probe being coated with gel", no color image is displayed in an ROI in an index value image in elastography corresponding to the current frame. In contrast to this, the conventional ultrasonic diagnostic apparatus cannot detect the "release state" of the ultrasonic probe. Even if, therefore, the ultrasonic probe is in the "release state", a color image is displayed in the ROI in an index value image in elastography corresponding to the current frame, as shown in FIG. 7A.

(Modification)

The ultrasonic diagnostic apparatus according to the first embodiment calculates average values in ROIs and the difference value between each combination of average values in the respective frames in a predetermined period. The apparatus then controls execution/non-execution of color display of an index value image based on the calculation result. In contrast to this, the ultrasonic diagnostic apparatus according to this modification sets a plurality of local regions in an ROI and calculates the average value of movement velocities in each local region and the difference value between average values in corresponding local regions for each combination between the respective frames in a predetermined period. The apparatus then controls execution/non-execution of color display with respect to each local region in an index value image based on the calculation result.

Figure 8:
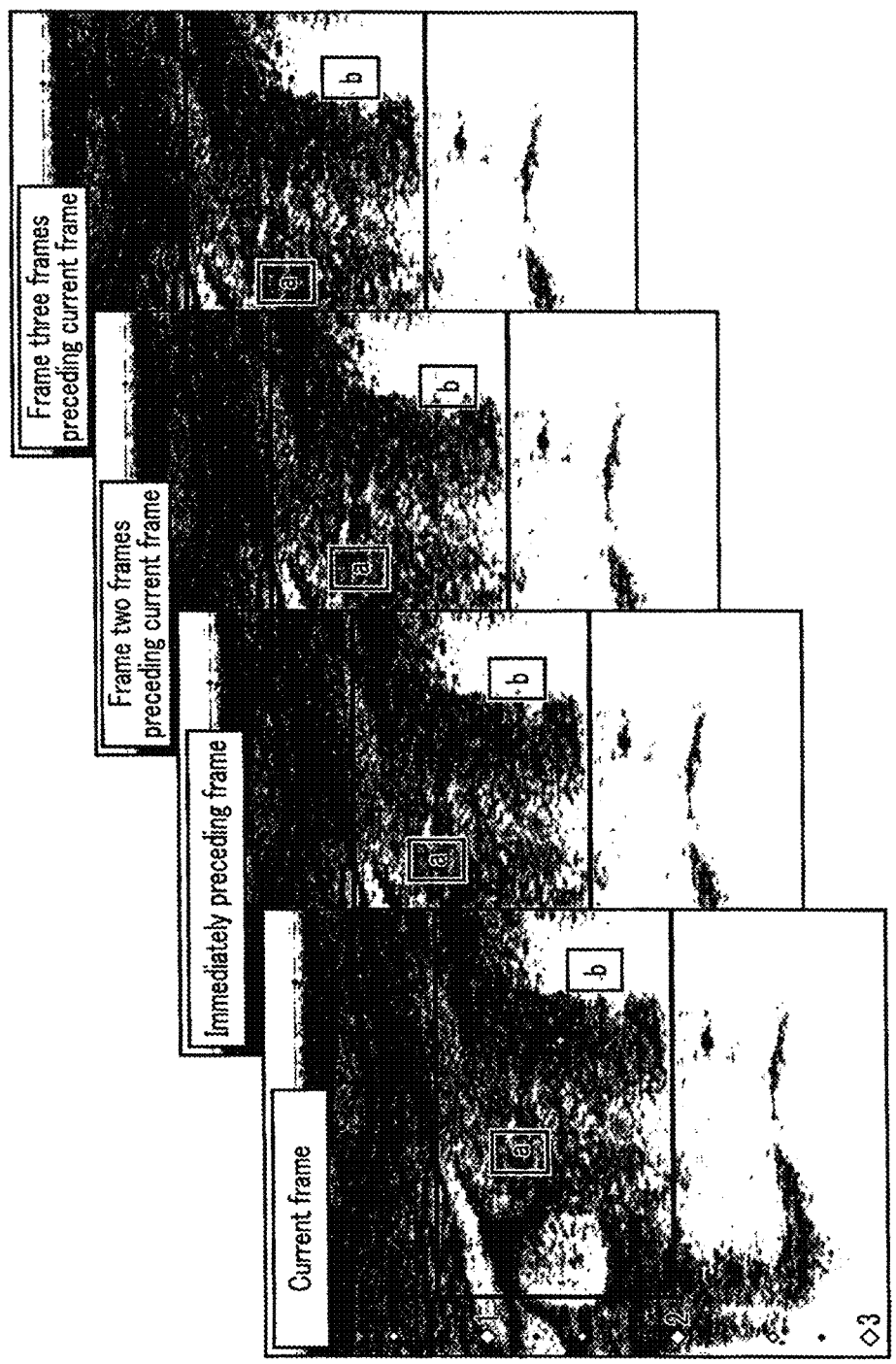
FIG. 8 is a view showing local regions a and b set in an ROI in an index value image corresponding to the current frame and local regions a and b set in ROIs in index value images corresponding to the respective three frames preceding the current frame.
Figure 13A:
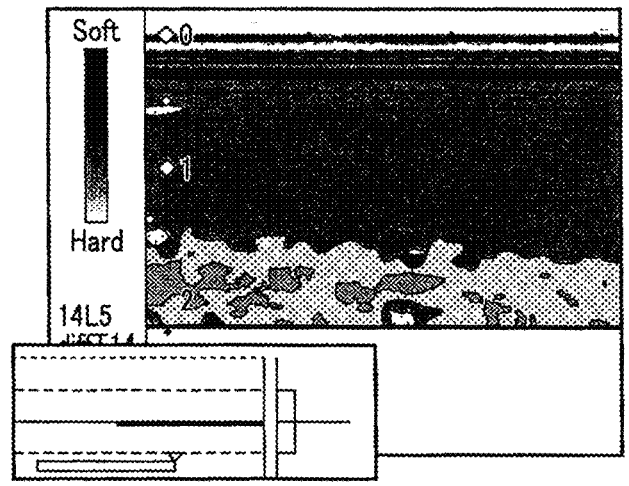
FIGS. 13A and 13B are views for explaining conventional elastography.
Figure 13B:
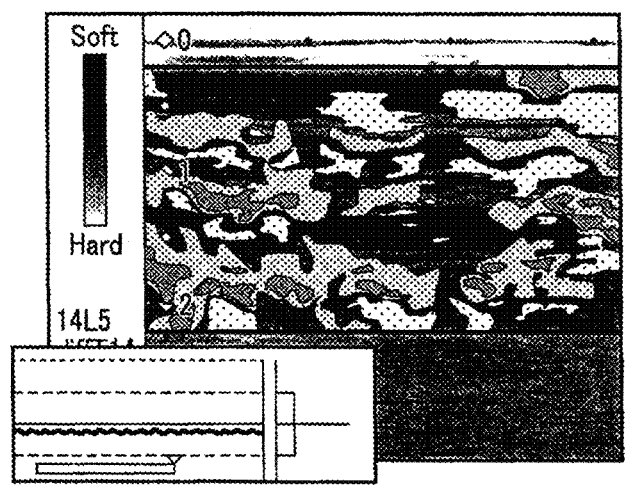
Figure 14:
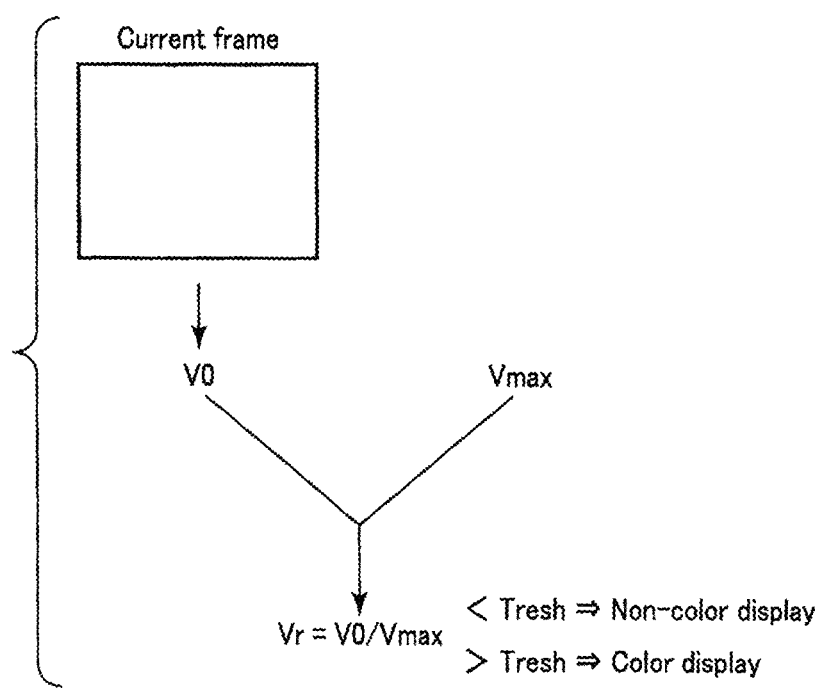
FIG. 14 is a view for explaining conventional elastography.

FIG. 8 is a view showing local regions a and b set in an ROI in an index value image corresponding to the current frame and local regions a and b set in an ROI in each of index value images corresponding to the three frames preceding the current frame.

The probe state detection circuitry 37 obtains index value images corresponding to four frames, of time-serially obtained index value images, which are obtained over a predetermined period (step S11 in FIG. 3). The probe state detection circuitry 37 sets an ROI in each of a plurality of index value images corresponding to the obtained four frames and calculates an average velocity in each local region in each ROI (step S12 in FIG. 3). Note that in the case shown in FIG. 8, the average velocity in the local region a in the current frame is represented by V0a, and the average velocities in the local regions a in the respective frames are respectively represented by V1a, V2a, and V3a as the frames go back from the current frame one by one. Likewise, the average velocity in the local region b in the current frame is represented by V0b, and the average velocities in the local regions b in the respective frames are respectively represented by V1b, V2b, and V3b as the frames go back from the current frame one by one.

The probe state detection circuitry 37 extracts desired m (m is an integer satisfying 1≤m≤4C2) combinations of two of V0a, V1a, V2a, and V3a (V0b, V1b, V2b, and V3b) corresponding to the four frames, and calculates the absolute value of the difference value between extracted each combination (pair) of average velocities (steps S12 and S13) in FIG. 3. If, for example, m=4C2=6, the probe state detection circuitry 37 extracts all combinations by using V0a, V1a, V2a, and V3a (V0b, V1b, V2b, and V3b) corresponding to the four frames, and calculates the difference values between average velocities corresponding to all the combinations in each of the local regions a and b.

The probe state detection circuitry 37 then compares each difference value corresponding to each combination with the predetermined threshold T in each of the local regions a and b, and determines based on the results whether there is one or more difference values equal to or more than the predetermined threshold T (step S15 in FIG. 3). If all the difference values corresponding to all the combinations are smaller than the threshold T, the probe state detection circuitry 37 determines that the corresponding local region is a "living tissue having no distortion", and sends out a signal indicating the corresponding information to the control processing circuitry 31 (NO in step S15 in FIG. 3). In contrast, if all the difference values corresponding to all the combinations include at least one difference value equal to or more than the predetermined threshold, the probe state detection circuitry 37 determines that the corresponding local region is a "living tissue having distortion", and sends out a signal indicating the corresponding information to the control processing circuitry 31 (YES in step S15 in FIG. 3).

More specifically, assume that with regard to the magnitude relations between the respective difference values corresponding to the respective combinations and the predetermined threshold T in the local region a, five difference values |V0a–V1a|, |V0a–V3a|, |V1a–V2a|, |V1a–V3a|, and |V2a–V3a| of all the six combinations exceed the predetermined threshold T, as shown in FIG. 9A. In this case, since there are one or more difference values larger than the predetermined threshold T, the probe state detection circuitry 37 determines that the corresponding region is a "living tissue having distortion", and sends out a signal indicating the corresponding information to the control processing circuitry 31.

In contrast, assume that with regard to the magnitude relations between the respective difference values corresponding to the respective combinations and the predetermined threshold T in the local region b, all the difference values corresponding to all the six combinations are smaller than the predetermined threshold T, as shown in FIG. 9B. In this case, since there is no difference value larger than the predetermined threshold T, the probe state detection circuitry 37 determines that the region is a "living tissue having no distortion", and sends out a signal indicating the corresponding information to the control processing circuitry 31.

With regard to the local region a (or a region including a region near the local region a) regarding which a signal indicating that the region is a "living tissue having distortion" is received from the probe state detection circuitry 37, the control processing circuitry 31 controls the display processing circuitry 30 so as to display a color image in the logical region a in the ROI in an index value image in elastography corresponding to the current frame (step S16 in FIG. 3). With regard to the local region b (or a region including a region near the local region b) regarding which a signal indicating that the region is a "living tissue having no distortion" is received from the probe state detection circuitry 37, the control processing circuitry 31 controls the display processing circuitry 30 so as not to display any color image in the logical region b in the ROI in an index value image in elastography corresponding to the current frame (step S17 in FIG. 3).

As shown in FIG. 11, according to this modification, with regard to the local region b detected as a "living tissue having no distortion", the local region b is not displayed in color in the ROI in an index value image in elastography corresponding to the current frame.

In contrast to this, as shown in FIG. 10, the conventional ultrasonic diagnostic apparatus displays a color image in the local region b in the ROI in the index value image in elastography corresponding to the current frame.

Note that the local region b determined as a "living tissue having no distortion" can be regarded as a region in the bronchi, blood vessel, or the like. Color display in elastography is implemented by relatively mapping index values (e.g., distortion values) in an ROI set in an index value image. According to this modification, distortion in a region in which the movement of the tissue is detected can be calculated with higher accuracy by calculating index values excluding those in a region in the bronchi, blood vessel, or the like, such as the local region b.

The following effects can be obtained by the above arrangement.

Assume that this ultrasonic diagnostic apparatus has detected the release state by discriminating and detecting the release state of the ultrasonic probe and the non-release state in which, for example, an ultrasonic image is obtained by using the ultrasonic probe while manual vibration is applied to a diagnosis region. In this case, the apparatus executes display control so as to set "non-execution" for color display of an index value image in an ultrasonic image displayed as an elastography image upon detection of the release state. This can therefore avoid a situation in which color display of an index value image is executed in spite of the fact that the ultrasonic probe is in the release state. This can solve the problem of making a user or patient feel anxiety about image diagnosis using ultrasonic elastography.

In addition, this ultrasonic diagnostic apparatus sets a plurality of local regions in an elastography ROI instead of using the average value of velocities in the entire ROI, and calculates the average value of index values in each local region and the difference value between the average values in local regions for each combination between the respective frames in a predetermined period. Based on this result, execution/non-execution of color display of an index value image is locally controlled. This makes it possible to control execution/non-execution of color display of an index value image with reference to each local region.

Second Embodiment

An ultrasonic diagnostic apparatus according to the second embodiment will be described next. The ultrasonic diagnostic apparatus according to this embodiment discriminates and detects the release state and non-release state of the ultrasonic probe, and executes control concerning transmission from the ultrasonic probe, such as decreasing power (e.g., a driving voltage or a driving frequency) to be supplied to the ultrasonic probe upon detection of the release state.

FIG. 12 is a flowchart showing a display control procedure using a probe state detection function according to the second embodiment. Processing in each step will be described below with reference to FIG. 12.

Time-series index value images are sequentially obtained in accordance with a predetermined frame rate by ultrasonic transmission/reception executed in response to the input of an imaging start instruction in step S1 in FIG. 2 as a trigger. A probe state detection circuitry 37 obtains n (n is an integer satisfying n≥3) reception signals, of the time-serially obtained reception signals (or luminance information at the same position in a B-mode image or the like), which correspond to the same position in an ultrasonic scanning slice obtained over a predetermined period (step S21). Note that the n reception signals are preferably temporally continuous but are not limited to it, as described above.

The probe state detection circuitry 37 extracts desired m (m is an integer satisfying 1≤m≤nC2) combinations of two reception signals of the obtained n reception signals, and calculates the absolute values of the difference values between the extracted combinations (pairs) of reception signals (steps S22 and S23). The probe state detection circuitry 37 compares each difference value corresponding to each combination obtained in step S23 with a predetermined threshold T, and determines, based on the comparison results, whether there are one or more difference values larger than the predetermined threshold T (step S24). If the determination result indicates that all the difference values corresponding to all the combinations are smaller than the predetermined threshold T, the probe state detection circuitry 37 determines that "the release state of the ultrasonic probe is detected", and sends out a signal indicating the corresponding information to a control processor 31 (NO in step S24=(the ultrasonic probe) remaining still). On the other hand, if at least one of all the difference values corresponding to all the combinations exceeds the predetermined threshold, the probe state detection circuitry 37 determines that "the release state of the ultrasonic probe is not detected", and sends out a signal indicating the corresponding information to the control processing circuitry 31 (YES in step S24=(the ultrasonic probe) moving).

Upon reception of the signal indicating that "the release state of the ultrasonic probe is not detected" from the probe state detection circuitry 37, the control processing circuitry 31 controls an ultrasonic transmission circuitry 21 so as to maintain the transmission power of an ultrasonic probe 12 set in the ultrasonic diagnostic apparatus (step S25). In contrast to this, upon reception of the signal indicating that "the release state of the ultrasonic probe is detected" from the probe state detection circuitry 37, the control processing circuitry 31 controls the ultrasonic transmission circuitry 21 so as to weaken the transmission power of the ultrasonic probe 12 set in the ultrasonic diagnostic apparatus (step S26).

Note that the probe state detection function according to this embodiment is repeatedly executed concurrently with processing in steps S2 and S3 in response to the input of an imaging start instruction in step S1 as a trigger to execute control concerning the transmission power of the ultrasonic probe 12.

In addition, obviously, control concerning transmission from the ultrasonic probe using this probe state detection function can also be executed in addition to display control using the probe state detection function described in the first embodiment.

The ultrasonic diagnostic apparatus described above discriminates and detects the release state of the ultrasonic probe and the non-release state in which, for example, an ultrasonic image is obtained by using the ultrasonic probe while manual vibration is applied to a diagnosis region. Upon detecting the release state, this apparatus executes control concerning transmission from the ultrasonic probe, for example, decreasing power to be supplied to the ultrasonic probe. Assume that the user releases the ultrasonic probe in the air while forgetting about performing a freeze operation. In this case, if the ultrasonic probe is continuously released in the air, it may promote deterioration in the probe. This apparatus can automatically decrease the transmission power of the ultrasonic probe. This can prevent promotion of deterioration in the ultrasonic probe as compared with the conventional ultrasonic diagnostic apparatus.

Third Embodiment

An ultrasonic diagnostic apparatus according to the third embodiment will be described next. The first and second embodiments each have exemplified the ultrasonic diagnostic apparatus which discriminates and detects the release state and non-release state of the ultrasonic probe based on average velocities or the like in the respective ROIs set in time-serially obtained index value images. The third embodiment will exemplify an ultrasonic diagnostic apparatus which discriminates and detects the release state and non-release state of the ultrasonic probe based on the position of the ultrasonic probe.

FIG. 15 is a block diagram showing the arrangement of an ultrasonic diagnostic apparatus 1A according to this embodiment. As shown in FIG. 15, the ultrasonic diagnostic apparatus 1A includes an ultrasonic diagnostic apparatus main body 11, an ultrasonic probe 12, an input device 13, and a monitor 14. The ultrasonic diagnostic apparatus main body 11 includes an ultrasonic transmission circuitry 21, an ultrasonic reception circuitry 22, a B-mode processing circuitry 23, a blood flow detection circuitry 24, a raw data memory 25, a volume data generation circuitry 26, an image processing circuitry 28, a display processing circuitry 30, a control processing circuitry 31, a memory 32, an interface unit 33, an index value image generation circuitry 35, and an probe state detection circuitry 37A. A scanning slice position sensor 41 is connected to the ultrasonic diagnostic apparatus 1A. The function of each constituent element will be described below.

A magnetic field generator 39 is provided near an object. The magnetic field generator 39 generates a magnetic field for the calculation of the position of a scanning slice by the scanning slice position sensor 41 provided on the ultrasonic probe 12. The position of the magnetic field generator 39 is stored in the memory 32 in advance.

The scanning slice position sensor 41 is provided at a predetermined position on the ultrasonic probe 12. The scanning slice position sensor 41 is, for example, a magnetic sensor. The scanning slice position sensor 41 detects a magnetic field generated by the magnetic field generator 39, and calculates the position of a scanning slice based on the detected magnetic field. The calculated position of the scanning slice is sent out in real time into the apparatus main body 11 via the interface unit 33.

The probe state detection circuitry 37A is constituted by, for example, a predetermined processor and a memory. The probe state detection circuitry 37A discriminates and detects the release state and non-release state of the ultrasonic probe based on the position of the scanning slice sent out in real time from the scanning slice position sensor 41. The operation of the probe state detection circuitry 37A will be described in detail later.

Figure 16:
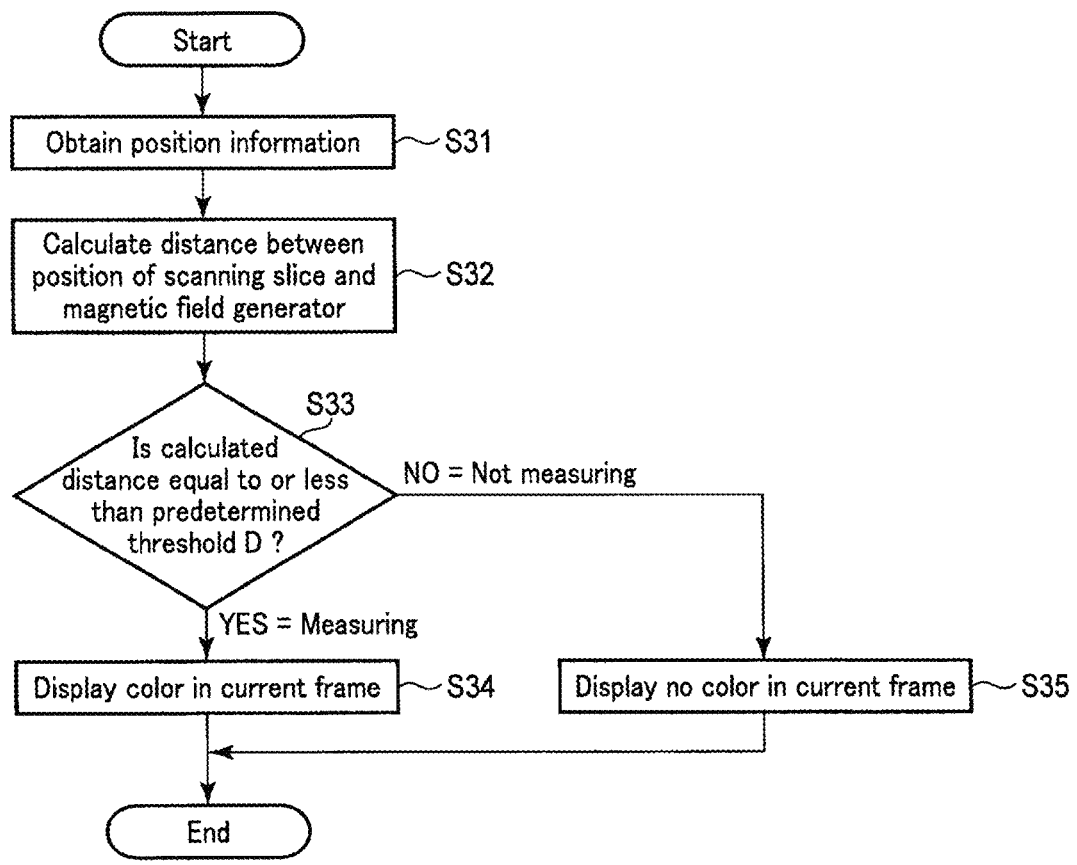
FIG. 16 is a flowchart showing a display control procedure using a probe state detection function according to the third embodiment.

FIG. 16 is a flowchart showing a display control procedure using a probe state detection function according to the third embodiment. Processing in each step will be described below with reference to FIG. 16.

Time-series index value images are sequentially obtained at a predetermined frame rate by ultrasonic transmission/reception executed in response to the input of an imaging start instruction in step S1 in FIG. 2 as a trigger.

In addition, the magnetic field generator 39 starts generating a magnetic field in response to the input of the imaging start instruction in step S1 as a trigger. The scanning slice position sensor 41 starts detecting a magnetic field and calculating the position of a scanning slice in response to the input of the imaging start instruction in step S1 as a trigger.

The probe state detection circuitry 37A obtains the position of the scanning slice sent out in real time from the scanning slice position sensor 41 (step S31).

The probe state detection circuitry 37A calculates the distance between the magnetic field generator 39 and the ultrasonic probe 12 based on the obtained position of the scanning slice and the position of the magnetic field generator 39 stored in the memory 32 (step S32).

The probe state detection circuitry 37A determines whether the distance between the magnetic field generator 39 and the ultrasonic probe 12 is equal to or less than a predetermined threshold D (step S33).

Upon determining that the distance between the magnetic field generator 39 and the ultrasonic probe 12 is equal to or less than the predetermined threshold D, the probe state detection circuitry 37A determines that "the release state of the ultrasonic probe is not detected", and sends out a signal indicating the corresponding information to the control processing circuitry 31 (YES in step S33=measuring).

Upon determining that the distance between the magnetic field generator 39 and the ultrasonic probe 12 exceeds the predetermined threshold D, the probe state detection circuitry 37A determines that "the release state of the ultrasonic probe is detected", and sends out a signal indicating the corresponding information to the control processing circuitry 31 (YES in step S33=not measuring).

Upon receiving the signal indicating that "the release state of the ultrasonic probe is not detected" from the probe state detection circuitry 37A, the control processing circuitry 31 controls the display processing circuitry 30 so as to display a color image in the ROI in the index value image in elastography corresponding to the current frame (step S34). In contrast, upon receiving the signal indicating that "the release state of the ultrasonic probe is detected" from the probe state detection circuitry 37A, the control processing circuitry 31 controls the display processing circuitry 30 so as not to display any color image in the ROI in the index value image in elastography corresponding to the current frame (step S35).

In addition, obviously, display control using this probe state detection function can also be executed in addition to control concerning transmission from the ultrasonic probe described in the second embodiment.

Assume that this ultrasonic diagnostic apparatus has detected the release state by discriminating and detecting the release state of the ultrasonic probe and the non-release state in which, for example, an ultrasonic image is obtained by using the ultrasonic probe while manual vibration is applied to a diagnosis region, based on the distance between the position of the magnetic field generator provided near an object and the position of a slice scanned by the ultrasonic probe. In this case, the apparatus executes display control so as to set "non-execution" for color display of an index value image in an ultrasonic image displayed as an elastography image. This can therefore avoid a situation in which color display of an index value image is executed in spite of the fact that the ultrasonic probe is in the release state. This can solve the problem of making a user or patient feel anxiety about image diagnosis using ultrasonic elastography.

Note that according to the above description, the release state of the ultrasonic probe is detected based on a result of comparing the distance between the magnetic field generator 39 and the ultrasonic probe 12 and the predetermined threshold D. However, this is not exhaustive. For example, the release state of the ultrasonic probe may be detected based on the position of the ultrasonic probe 12 relative to a predetermined reference position.

Fourth Embodiment

An ultrasonic diagnostic apparatus according to the fourth embodiment will be described next. The third embodiment has exemplified the ultrasonic diagnostic apparatus which discriminates and detects the release state and non-release state of the ultrasonic probe based on the position of the ultrasonic probe. The fourth embodiment will exemplify an ultrasonic diagnostic apparatus which discriminates and detects the release state and non-release state of the ultrasonic probe based on the posture of the ultrasonic probe and the elapsed time during which the ultrasonic probe is maintained in a predetermined posture.

FIG. 17 is a block diagram showing the arrangement of an ultrasonic diagnostic apparatus 1B according to this embodiment. As shown in FIG. 17, the ultrasonic diagnostic apparatus 1B includes an ultrasonic diagnostic apparatus main body 11, an ultrasonic probe 12, an input device 13, and a monitor 14. The ultrasonic diagnostic apparatus main body 11 includes an ultrasonic transmission circuitry 21, an ultrasonic reception circuitry 22, a B-mode processing circuitry 23, a blood flow detection circuitry 24, a raw data memory 25, a volume data generation circuitry 26, an image processing circuitry 28, a display processing circuitry 30, a control processing circuitry 31, a memory 32, an interface unit 33, an index value image generation circuitry 35, and a probe state detection circuitry 37B. A scanning slice posture sensor 43 is connected to the ultrasonic diagnostic apparatus 1B. The function of each constituent element will be described below.

The scanning slice posture sensor 43 is provided at a predetermined position on the ultrasonic probe 12. The scanning slice posture sensor 43 is, for example, a gyro sensor. The scanning slice posture sensor 43 holds preset reference posture information. The scanning slice posture sensor 43 detects an angular velocity generated by the movement of the ultrasonic probe 12. The scanning slice posture sensor 43 calculates the posture of a slice scanned by the ultrasonic probe 12 based on the reference posture information and the detected angular velocity. The calculated posture of the scanning slice is sent out in real time into the apparatus main body 11 via the interface unit 33.

The probe state detection circuitry 37B is constituted by, for example, a predetermined processor and a memory. The probe state detection circuitry 37B discriminates and detects the release state and non-release state of the ultrasonic probe based on the posture of the scanning slice sent out in real time from the scanning slice posture sensor 43. The operation of the probe state detection circuitry 37B will be described in detail later.

FIG. 18 is a flowchart showing a display control procedure using a probe state detection function according to the fourth embodiment. Processing in each step will be described below with reference to FIG. 18.

Time-series index value images are sequentially obtained at a predetermined frame rate by ultrasonic transmission/reception executed in response to the input of an imaging start instruction in step S1 in FIG. 2 as a trigger.

In addition, the scanning slice posture sensor 43 starts detecting an angular velocity and calculating the posture of a scanning slice in response to the input of an imaging start instruction in step S1 as a trigger.

The probe state detection circuitry 37B obtains the posture of a scanning slice sent out in real time from the scanning slice posture sensor 43 (step S41).

The probe state detection circuitry 37B determines whether the obtained posture of the scanning slice is upward (step S42). "Upward" is, for example, a state in which the angle defined by the axis of the ultrasonic probe 12 and a vertical direction is equal or less than a predetermined angle.

Upon determining that the posture of the scanning slice is not upward, the probe state detection circuitry 37B determines that "the release state of the ultrasonic probe is not detected", and sends out a signal indicating the corresponding information to the control processing circuitry 31 (NO in step S42=measuring).

Upon determining that the posture of the scanning slice is upward, the probe state detection circuitry 37B determines whether the posture of the scanning slice is kept in an upward state for a predetermined period of time or more (step S43).

If the posture of the scanning slice is kept in the upward state for the predetermined period of time or more, the probe state detection circuitry 37B determines that "the release state of the ultrasonic probe is detected", and sends out a signal indicating the corresponding information to the control processing circuitry 31 (YES in step S43=not measuring).

If the posture of the scanning slice is not kept in the upward state for the predetermined period of time and has changed into another posture, the probe state detection circuitry 37B determines that "the release state of the ultrasonic probe is not detected", and sends out a signal indicating the corresponding information to the control processing circuitry 31 (NO in step S43=measuring).

Upon receiving the signal indicating that "the release state of the ultrasonic probe is not detected" from the probe state detection circuitry 37B, the control processing circuitry 31 controls the display processing circuitry 30 so as to display a color image in the ROI in an index value image in elastography corresponding to the current frame (step S44). In contrast, upon receiving the signal indicating that "the release state of the ultrasonic probe is detected" from the probe state detection circuitry 37B, the control processing circuitry 31 controls the display processing circuitry 30 so as not to display any color image in the ROI in an index value image in elastography corresponding to the current frame (step S45).

In addition, obviously, display control using the probe state detection function can also be executed in addition to control concerning transmission from the ultrasonic probe described in the second embodiment.

Assume that this ultrasonic diagnostic apparatus has detected the release state of the ultrasonic probe by discriminating and detecting the release state and non-release state of the ultrasonic probe based on the posture of the ultrasonic probe and the elapsed time during which the ultrasonic probe is maintained in a predetermined posture. In this case, the apparatus executes display control so as to set "non-execution" for color display of an index value image in an ultrasonic image displayed as an elastography image. This can therefore avoid a situation in which color display of an index value image is executed in spite of the fact that the ultrasonic probe is in the release state. This can solve the problem of making a user or patient feel anxiety about image diagnosis using ultrasonic elastography.

Fifth Embodiment

This embodiment will exemplify an ultrasonic diagnostic apparatus which discriminates and determines the release state and non-release state of an ultrasonic probe based on the transmission/reception state of the ultrasonic probe and whether the ultrasonic probe is accommodated in a holder.

Figure 19:
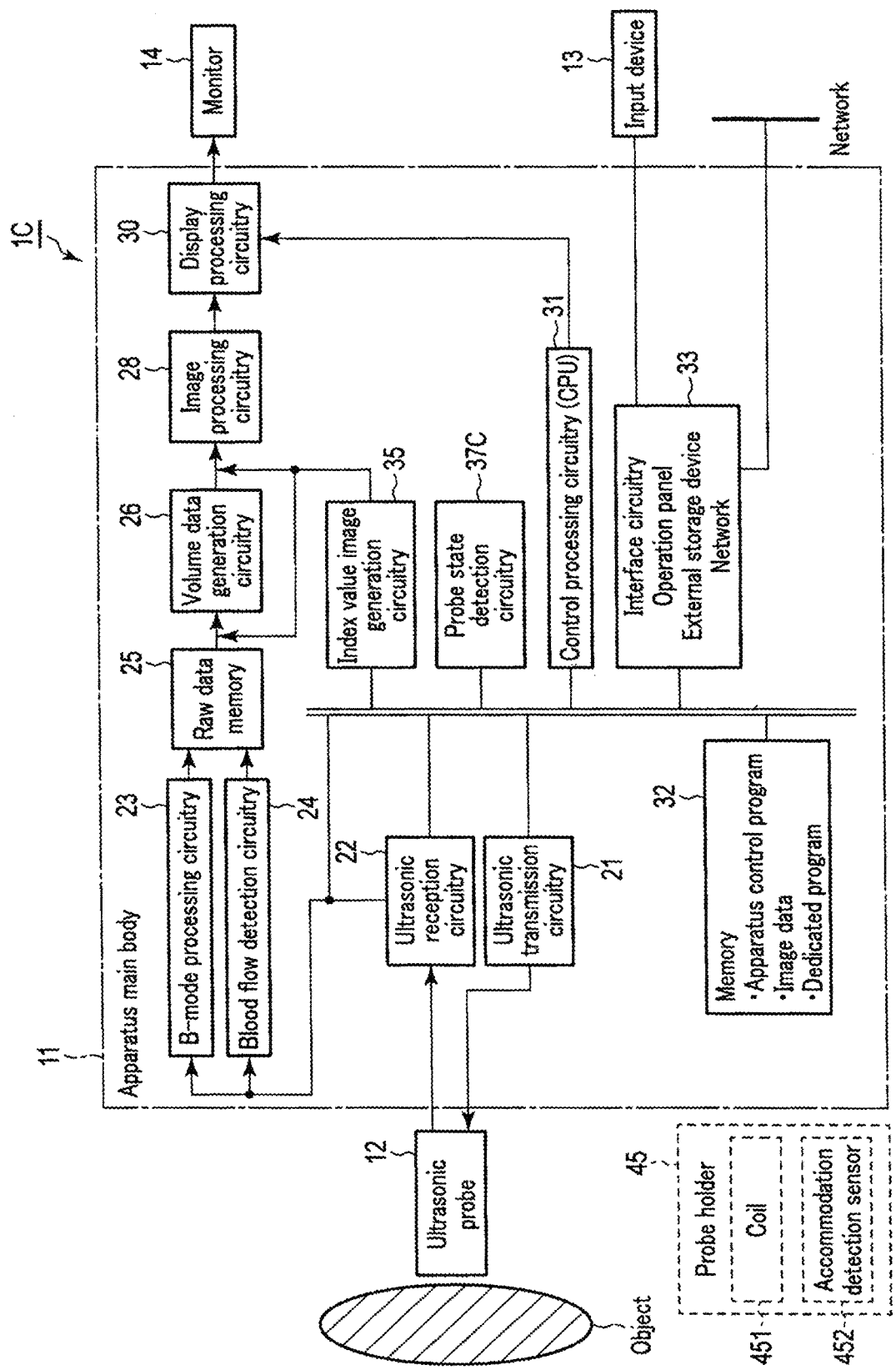
FIG. 19 is a block diagram showing the arrangement of an ultrasonic diagnostic apparatus according to the fifth embodiment.

FIG. 19 is a block diagram showing the arrangement of an ultrasonic diagnostic apparatus 1C according to this embodiment. As shown in FIG. 19, the ultrasonic diagnostic apparatus 1C includes an ultrasonic diagnostic apparatus main body 11, an ultrasonic probe 12, an input device 13, and a monitor 14. The ultrasonic diagnostic apparatus main body 11 includes an ultrasonic transmission circuitry 21, an ultrasonic reception circuitry 22, a B-mode processing circuitry 23, a blood flow detection circuitry 24, a raw data memory 25, a volume data generation circuitry 26, an image processing circuitry 28, a display processing circuitry 30, a control processing circuitry 31, a memory 32, an interface unit 33, an index value image generation circuitry 35, and a probe state detection circuitry 37C. A probe holder 45 is provided near the apparatus main body 11. An IC card chip storing a probe ID is attached to the ultrasonic probe 12. Note that in the following description, a plurality of ultrasonic probes 12 are provided. The function of each constituent element will be described below.

The memory 32 stores probe information of the plurality of ultrasonic probes 12. The probe information includes a probe ID corresponding to each of the plurality of ultrasonic probes 12.

The probe holder 45 is provided near the apparatus main body 11. The probe holder 45 accommodates the ultrasonic probes 12 which are not used for imaging. In addition, the probe holder 45 temporarily accommodates the ultrasonic probe 12 during imaging. The probe holder 45 includes a coil 451 for generating a dielectric electromotive force accompanying the movement of the ultrasonic probe 12 to the probe holder 45. The probe holder 45 also includes an accommodation detection sensor 452.

The accommodation detection sensor 452 detects the ultrasonic probe 12 based on a change in dielectric electromotive force accompanying the movement of the ultrasonic probe 12 to the probe holder 45 in response to when the ultrasonic probe 12 is accommodated in the probe holder 45. The accommodation detection sensor 452 identifies the ultrasonic probe 12 by reading, using the coil 451, the probe ID stored in an IC card chip attached to the ultrasonic probe 12.

Information indicating that the ultrasonic probe 12 has been detected and the probe ID of the ultrasonic probe 12 are sent out in real time into the apparatus main body 11 via the interface unit 33.

The probe state detection circuitry 37C is constituted by, for example, a predetermined processor and a memory. The probe state detection circuitry 37C discriminates and detects the release state and non-release state of the ultrasonic probe based on the information indicating the detection of the ultrasonic probe 12 and the probe ID of the ultrasonic probe 12, which are sent out in real time from the accommodation detection sensor 452. The probe state detection circuitry 37C monitors the ultrasonic transmission circuitry 21 and the ultrasonic reception circuitry 22 and obtains an ultrasonic transmission/reception state. The operation of the probe state detection circuitry 37C will be described in detail later.

Figure 20:
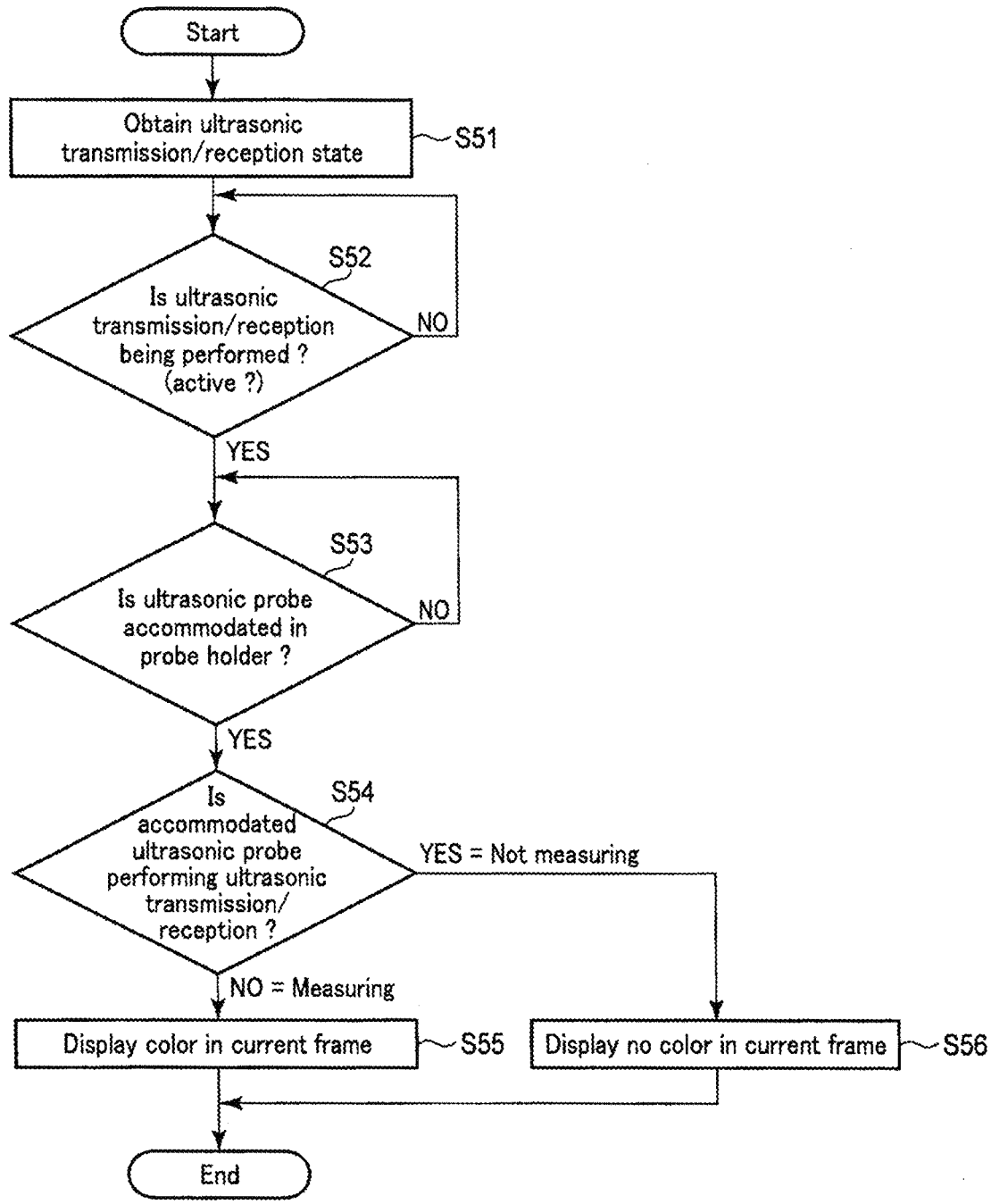
FIG. 20 is a flowchart showing a display control procedure using a probe state detection function according to the fifth embodiment.

FIG. 20 is a flowchart showing a display control procedure using the probe state detection function according to the fifth embodiment. Processing in each step will be described below with reference to FIG. 20.

Time-series index value images are sequentially obtained at a predetermined frame rate by ultrasonic transmission/reception executed in response to the input of an imaging start instruction in step S1 in FIG. 2 as a trigger.

The probe state detection circuitry 37C monitors the ultrasonic transmission circuitry 21 and the ultrasonic reception circuitry 22 in response to the input of an imaging start instruction in step S1 as a trigger (step S51).

The probe state detection circuitry 37C determines whether an ultrasonic transmission/reception state is a state in which ultrasonic transmission/reception is being performed step S52).

If the ultrasonic transmission/reception state is a state in which ultrasonic transmission/reception is being performed (YES in step S52), the probe state detection circuitry 37C determines whether the ultrasonic probe 12 is accommodated in the probe holder 45, based on the information indicating that the ultrasonic probe 12 has been detected, which is sent out in real time from the accommodation detection sensor 452 (step S53). At this time, the probe state detection circuitry 37C reads out, from the memory 32, a probe ID corresponding to the ultrasonic probe 12 which is performing ultrasonic transmission/reception.

Upon determining that the ultrasonic probe 12 is accommodated in the probe holder 45 (YES in step S53), the probe state detection circuitry 37C determines whether the ultrasonic probe 12 is performing ultrasonic transmission/reception, by comparing the probe ID sent out from the accommodation detection sensor 452 with a probe ID corresponding to the ultrasonic probe 12 which is performing ultrasonic transmission/reception (step S54).

If the accommodated ultrasonic probe 12 is not performing ultrasonic transmission/reception, the probe state detection circuitry 37C determines that "the release state of the ultrasonic probe is not detected", and sends out a signal indicating the corresponding information to the control processing circuitry 31 (NO in step S54=measuring).

If the accommodated ultrasonic probe 12 is performing ultrasonic transmission/reception, the probe state detection circuitry 37C determines that "the release state of the ultrasonic probe is detected", and sends out a signal indicating the corresponding information to the control processing circuitry 31 (YES in step S54=not measuring).

Upon receiving the signal indicating that "the release state of the ultrasonic probe is not detected" from the probe state detection circuitry 37C, the control processing circuitry 31 controls the display processing circuitry 30 so as to display a color image in the ROI in an index value image in elastography corresponding to the current frame (step S55). In contrast, upon receiving the signal indicating that "the release state of the ultrasonic probe is detected" from the probe state detection circuitry 37C, the control processing circuitry 31 controls the display processing circuitry 30 so as not to display any color image in the ROI in the index value image in elastography corresponding to the current frame (step S56).

In addition, obviously, display control using the probe state detection function can also be executed in addition to control concerning transmission from the ultrasonic probe described in the second embodiment.

Assume that this ultrasonic diagnostic apparatus has detected the release state of the ultrasonic probe by discriminating and detecting the release state and non-release state of the ultrasonic probe based on the transmission/reception state of the ultrasonic probe and whether the ultrasonic probe is accommodated in the holder. In this case, the apparatus executes display control so as to set "non-execution" for color display of an index value image in an ultrasonic image displayed as an elastography image. This can therefore avoid a situation in which color display of an index value image is executed in spite of the fact that the ultrasonic probe is in the release state. This can solve the problem of making a user or patient feel anxiety about image diagnosis using ultrasonic elastography.

Note that the present invention is not limited to the embodiments described above, and constituent elements can be modified and embodied in the execution stage within the spirit and scope of the invention. The following are concrete modifications.

(1) In addition, each function according to each embodiment described above can be implemented by installing programs for executing the above processing in a computer such as a workstation and loading them in the memory. In this case, the programs which can cause the computer to execute the above method can be distributed by being stored in recording media such as magnetic disks (floppy disks, hard disks, and the like), optical disks (CD-ROMs, DVDs, and the like), and semiconductor memories.

(2) Each embodiment described above has exemplified the case in which a two-dimensional region (two-dimensional slice) is a target for elastography. However, a three-dimensional region can also be a target. In this case, a three-dimensional region is volume-scanned, and the above probe state detection is executed by using a three-dimensional ROI. Based on this detection result, at least one of control concerning color display of an index value image and control concerning transmission from the ultrasonic probe may be executed.

(3) Each embodiment described above has exemplified the case in which the probe state detection function is applied to elastography using a B-mode image as a tissue structure image and an index value image generated by using the B-mode image. However, this is not exhaustive. For example, a tissue structure image and an index value image may be obtained in the tissue Doppler mode.

(4) It is preferable to arbitrarily change the predetermined threshold T used in determination in step S15 in FIG. 3 and step S24 in FIG. 12 in accordance with, for example, a velocity range (scale) or the like set in elastography. This can implement probe state detection in accordance with the strength of compression/release.

(5) In general, when transmission conditions for the ultrasonic probe change, offset components are also influenced. For this reason, in order to determine the movement of a tissue between frames, it is necessary to set the amount of change in signal value (pixel value) between frames as a reference instead of setting a signal value (or a pixel value) corresponding to the tissue as a reference. That is, in each embodiment described above, all the combinations using n frames obtained over a predetermined period are collected, and a difference is calculated for each combination, thereby comparing each difference with the predetermined threshold T. However, as long as the amount of change in signal value (or pixel value) between frames is set as a determination criterion, the present invention is not limited to the above embodiments. For example, the release state of the ultrasonic probe may be detected based on the magnitude relation between a predetermined threshold and the difference between the maximum and minimum values of the average velocities in ROIs corresponding to n frames obtained over a predetermined period.

(6) The third embodiment is configured to discriminate and detect the release state of the ultrasonic probe and the non-release state in which, for example, an ultrasonic image is obtained by using the ultrasonic probe while manual vibration is applied to a diagnosis region, based on the distance between the position of the magnetic field generator provided near the object and the position of a slice scanned by the ultrasonic probe 12. However, this is not exhaustive. For example, the probe state detection circuitry 37A obtains, via the input device 13, an image indicating the state of image diagnosis, including images of the ultrasonic probe and the object which are obtained by a camera or the like. The probe state detection circuitry 37A may calculate the distance between the position of a slice scanned by the ultrasonic probe and the position of the object based on the obtained image, and discriminate and detect the release state of the ultrasonic probe and the non-release state in which, for example, an ultrasonic image is obtained by using the ultrasonic probe while manual vibration is applied to a diagnosis region, based on the distance between the position of the scanning slice and the position of the object.

(7) Each embodiment described above is based on the premise that a B-mode image or the like is used as a tissue structure image. However, this is not exhaustive. For example, a tissue structure image may be an image obtained by a modality other than an ultrasonic diagnostic apparatus, such as an X-ray CT image.

(8) Each embodiment described above has exemplified the case in which the probe state detection function is applied to tissue elastic imaging. However, this is not exhaustive. The probe state detection function may be applied to other imaging methods such as a color Doppler method, attenuation imaging, parametric imaging, imaging using shear waves, and fusion imaging.

(9) The third to fifth embodiments may be arbitrarily combined. If, for example, the third and fourth embodiments are combined, the probe state detection function detects the release state of the ultrasonic probe in an active state based on the position and posture of the ultrasonic probe.

The word "processor" used in the above description means circuitry such as a CPU (Central Processing Unit), a GPU (Graphics Processing Unit), an ASIC (Application Specific Integrated Circuit), a programmable logic device (e.g., an SPLD (Simple Programmable Logic Device), a CPLD (Complex Programmable Logic Device), or an FPGA (Field Programmable Gate Array)), or the like. The processor implements functions by reading out programs stored in the storage circuit and executing the programs. Note that it is possible to directly incorporate programs in the circuit of the processor instead of storing the programs in the storage circuit. In this case, the processor implements functions by reading out programs incorporated in the circuit and executing the programs. Note that each processor in each embodiment described above may be formed as one processor by combining a plurality of independent circuits to implement functions as well as being formed as a single circuit for each processor. In addition, a plurality of constituent elements in each embodiment described above may be integrated into one processor to implement its function.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. An ultrasonic diagnostic apparatus comprising:
an ultrasonic probe used for ultrasound transmission/reception;
detection circuitry configured to detect a release state of the ultrasonic probe in an active state; and
processing circuitry configured to switch from a first control mode to a second control mode when the detection circuitry detects the release state of the ultrasonic probe during performing of the first control mode, wherein
the first control mode is for generating a first image based on an output from the ultrasonic probe, displaying a second image as an ultrasound image different from the first image, and displaying the first image with a predetermined opacity on the second image, and the second control mode is for displaying the second image without displaying the first image while generating the first image, wherein the first image comprises an image obtained by spatially distributing colors corresponding to physical amounts calculated by processing outputs from the ultrasonic probe, and the second image comprises an image obtained by spatially distributing luminance values calculated by processing outputs from the ultrasonic probe.

2. The apparatus of claim 1, wherein the index values relating to movement in the body of an object includes one of a velocity, a displacement, a distortion, and a distortion rate.

3. The apparatus of claim 1, wherein the detection circuitry detects the release state of the ultrasonic probe in the active state by processing outputs from the ultrasonic probe which correspond to a plurality of frames including a latest frame.

4. The apparatus of claim 3, wherein the detection circuitry calculates statistical values respectively corresponding to the plurality of frames by processing outputs from the ultrasonic probe, and detects the release state of the ultrasonic probe in the active state by threshold determination using a difference between a maximum value and a minimum value of the calculated statistical values.

5. The apparatus of claim 3, wherein the detection circuitry calculates statistical values respectively corresponding to the plurality of frames by processing outputs from the ultrasonic probe, and detects the release state of the ultrasonic probe based on the calculated statistical values.

6. The apparatus of claim 1, wherein the detection circuitry detects the release state of the ultrasonic probe in the active state based on a position of the ultrasonic probe.

7. The apparatus of claim 1, wherein the detection circuitry detects the release state of the ultrasonic probe in the active state based on a posture of the ultrasonic probe.

8. The apparatus of claim 1, wherein the detection circuitry detects the release state of the ultrasonic probe in the active state based on whether the ultrasonic probe is accommodated in a holder.

9. The apparatus of claim 1, wherein the detection circuitry detects the release state of the ultrasonic probe in the active state based on a position and a posture of the ultrasonic probe.

10. An ultrasonic diagnostic apparatus comprising:
an ultrasonic probe used for ultrasound transmission/reception;
detection circuitry configured to detect a release state of the ultrasonic probe in an active state; and
processing circuitry configured to switch from a first control mode to a second control mode when the detection circuitry detects the release state of the ultrasonic probe during performing of the first control mode, wherein the first control mode is for generating a first image based on an output from the ultrasonic probe, displaying a second image as an ultrasound image different from the first image, and displaying the first image with a predetermined opacity on the second image, and the second control mode is for generating the first image, displaying the second image, and displaying, on the second image, the first image with an opacity lower than the predetermined opacity, wherein the first image comprises an image obtained by spatially distributing colors corresponding to index values relating to movement in the body of an object calculated by processing outputs from the ultrasonic probe, and the second image comprises an image obtained by spatially distributing luminance values calculated by processing outputs from the ultrasonic probe.

11. The apparatus of claim 10, wherein the index values relating to movement in the body of an object includes one of a velocity, a displacement, a distortion, and a distortion rate.

12. The apparatus of claim 10, wherein the detection circuitry detects the release state of the ultrasonic probe in the active state by processing outputs from the ultrasonic probe which correspond to a plurality of frames including a latest frame.

13. The apparatus of claim 12, wherein the detection circuitry calculates statistical values respectively corresponding to the plurality of frames by processing outputs from the ultrasonic probe, and detects the release state of the ultrasonic probe in the active state by threshold determination using a difference between a maximum value and a minimum value of the calculated statistical values.

14. The apparatus of claim 12, wherein the detection circuitry calculates statistical values respectively corresponding to the plurality of frames by processing outputs from the ultrasonic probe, and detects the release state of the ultrasonic probe based on the calculated statistical values.

15. The apparatus of claim 10, wherein the detection circuitry detects the release state of the ultrasonic probe in the active state based on a position of the ultrasonic probe.

16. The apparatus of claim 10, wherein the detection circuitry detects the release state of the ultrasonic probe in the active state based on a posture of the ultrasonic probe.

17. The apparatus of claim 10, wherein the detection circuitry detects the release state of the ultrasonic probe in the active state based on whether the ultrasonic probe is accommodated in a holder.

18. The apparatus of claim 10, wherein the detection circuitry detects the release state of the ultrasonic probe in the active state based on a position and a posture of the ultrasonic probe.

* * * * *